US008859519B2

(12) United States Patent
Naar

(10) Patent No.: US 8,859,519 B2
(45) Date of Patent: Oct. 14, 2014

(54) METHODS TARGETING MIR-33 MICRORNAS FOR REGULATING LIPID METABOLISM

(75) Inventor: Anders M. Naar, Arlington, MA (US)

(73) Assignee: The General Hospital Corporation, Boston, MA (US)

(*) Notice: Subject to any disclaimer, the term of this patent is extended or adjusted under 35 U.S.C. 154(b) by 0 days.

(21) Appl. No.: 13/818,590

(22) PCT Filed: Aug. 25, 2011

(86) PCT No.: PCT/US2011/049207
§ 371 (c)(1),
(2), (4) Date: May 8, 2013

(87) PCT Pub. No.: WO2012/027601
PCT Pub. Date: Mar. 1, 2012

(65) Prior Publication Data
US 2013/0245093 A1 Sep. 19, 2013

Related U.S. Application Data

(60) Provisional application No. 61/377,077, filed on Aug. 25, 2010, provisional application No. 61/387,284, filed on Sep. 28, 2010.

(51) Int. Cl.
*A61K 48/00* (2006.01)
*C12N 15/113* (2010.01)
*A61K 31/7088* (2006.01)

(52) U.S. Cl.
CPC .......... *A61K 31/7088* (2013.01); *C12N 15/113* (2013.01); *C12N 2310/3231* (2013.01); *C12N 2310/113* (2013.01); *C12N 2310/14* (2013.01)
USPC .......................................... 514/44; 536/24.5

(58) Field of Classification Search
CPC ...................... C12N 2310/11; C12N 2310/141
See application file for complete search history.

(56) References Cited

U.S. PATENT DOCUMENTS

| 7,785,886 | B2 | 8/2010 | Hayden et al. |
| 2005/0059005 | A1 | 3/2005 | Tuschl et al. |
| 2005/0214793 | A1 | 9/2005 | Lawn et al. |
| 2005/0231319 | A1 | 10/2005 | Darr et al. |
| 2006/0058266 | A1 | 3/2006 | Manoharan et al. |
| 2008/0206232 | A1 | 8/2008 | Spiegelman et al. |
| 2010/0004320 | A1 | 1/2010 | Elmen et al. |
| 2011/0257244 | A1 | 10/2011 | Manoharan et al. |
| 2011/0281933 | A1 | 11/2011 | Baldan et al. |

FOREIGN PATENT DOCUMENTS

| WO | 03/029459 A2 | 4/2003 |
| WO | 2005/013901 A2 | 2/2005 |
| WO | 2007/027775 A2 | 3/2007 |
| WO | 2007/112754 A2 | 10/2007 |
| WO | 2008/061537 A2 | 5/2008 |
| WO | 2009/043353 A2 | 4/2009 |
| WO | 2010/133970 A1 | 11/2010 |
| WO | 2012/027704 A1 | 3/2012 |

OTHER PUBLICATIONS

Rayner et al. (Science 328: 1570-1573, Jun. 2010).*
Deckelbaum et al. (Arterosclerosis 4:225-231, May/Jun. 1984).*
Cullen et al. (American Journal of Cardiology Vo. 86, 2000).*
TargetScan: Prediction of microRNA targets, Release 4.2, Apr. 2008. "Predicted miRNA targets of miR-126/126-3p."
TargetScan: Prediction of microRNA targets, Release 4.2, Apr. 2008. "Predicted miRNA targets of miR-146."
Tavazoie et al., Nature, 451:147-154 (2007). "Endogenous human microRNAs that suppress breast cancer metastasis."
Tontonoz et al., Molecular Endocrinology, 17(6):985-993 (2003). "Liver X Receptor Signaling Pathways in Cardiovascular Disease."
Van Den Berg et al., Biochimica et Biophysica Acta, 1779:668-677 (2008). "RISC-target interaction: Cleavage and translational suppression."
Van Rooij et al., Trends in Genetics, 24(4):159-166 (2008). "MicroRNAs flex their muscles."
Vasudevan et al., Science, 318:1931-1934 (2007). "Switching from Repression to Activation: MicroRNAs Can Up-Regulate Translation."
Wang et al., The Journal of Clinical Investigation, 17(8):2216-2224 (2007). "Macrophage ABCA1 and ABCG1, but not SR-BI, promote macrophage reverse cholesterol transport in vivo."
Wang et al., Developmental Cell, 15:261-271 (2008). "The Endothelial-Specific MicroRNA miR-126 Governs Vascular Integrity and Angiogenesis."
Wang et al., PLoS One, 4(2):e4421 (2009). "Cepred: Predicting the Co-Expression Patterns of the Human Intronic microRNAs with Their Host Genes."
Williams et al., Current Opinion in Cell Biology, 21:461-469 (2009). "MicroRNA control of muscle development and disease."
Xiong et al., Biochemical and Biophysical Research Communications, 378:883-889 (2009). "Independent transcription of miR-281 in the intron of ODA in *Drosophila melanogaster*."
Yvan-Charvet et al., The Journal of Clinical Investigation, 117(12):3900-3908 (2007). "Combined deficiency of ABCA1 and ABCG1 promotes foam cell accumulation and accelerates atherosclerosis in mice."
Zelcer et al., PNAS, 104(25):10601-10606 (2007). "Attenuation of neuroinflammation and Alzheimer's disease pathology by liver x receptors."
Bartel et al., Cell, 136:215-233 (2009). "MicroRNAs: Target Recognition and Regulatory Functions."
Baskerville et al., RNA, 11:241-247 (2005). "Microarray profiling of microRNAs reveals frequent coexpression with neighboring miRNAs and host genes."
Brown et al., Cell, 89:331-340 (1997). "The SREBP Pathway: Regulation of Cholesterol Metabolism by Proteolysis of a Membrane-Bound Transcription Factor."
Chen et al., Nature Genetics, 38(2):228-233 (2006). "The role of microRNA-1 and microRNA-133 in skeletal muscle proliferation and differentiation."

(Continued)

*Primary Examiner* — Kimberly Chong
(74) *Attorney, Agent, or Firm* — Nixon Peabody LLP; David S. Resnick

(57) ABSTRACT

Compositions comprising nucleic acid sequences that target MiR-33a/b microRNAs are described, together with uses of the same in the treatment of certain disorders related to elevated serum triglyceride levels and obesity.

16 Claims, 7 Drawing Sheets

(56) References Cited

OTHER PUBLICATIONS

Davalos et al., PNAS, 108(22):9232-9237 (2011). "miR-33a/b contribute to the regulation of fatty acid metabolism and insulin signaling."

Davis et al., The Journal of Biological Chemistry, 279(32):33586-33592 (2004). "Niemann-Pick C1 Like 1 (NPC1L1) Is the Intestinal Phytosterol and Cholesterol Transporter and a Key Modulator of Whole-body Cholesterol Homeostasis."

De La Llera-Moya et al., Arterioscler Thromb Vasc. Biol., 30(4):796-801 Author Manuscript (2010). "The Ability to Promote Efflux via ABCA1 Determines the Capacity of Serum Specimens with Similar HDL-C to Remove Cholesterol from Macrophages."

Esau et al., Cell Metabolism, 3:87-98 (2006). "miR-122 regulation of lipid metabolism revealed by in vivo antisense targeting."

Fernandez-Hernando et al., Curr Opin Lipidol, 22(2):86-92 Author Manuscript (2011). "MicroRNAs in lipid metabolism."

Fish et al., Developmental Cell, 15:272-284 (2008). "miR-126 Regulates Angiogenic Signaling and Vascular Integrity."

Gao et al., IUBMB Life, 00(00):000-000 (2012). "Enemy of Partner: Relationship Between Intronic MicroRNAs and Their Host Genes."

GenBank Accession No. AJ421755 (Jun. 11, 2003).

Genbank Accession No. AJ550398 (Oct. 29, 2007).

Gerin et al., The Journal of Biological Chemistry, 285(44):33652-33661 (2010). "Expression of miR-33 from an SREBP2 Intron Inhibits Cholesterol Export and Fatty Acid Oxidation."

Griffiths-Jones et al., Nucleic Acids Research, 34:D140-144 (2006). "miRBase: microRNA sequences, targets and gene nomenclature."

Grimson et al., Molecular Cell, 27:91-105 with Supplemental Information (2007). "MicroRNA Targeting Specificity in Mammals: Determinants beyond See Pairing."

Horie et al., PNAS, 107(40):17321-17326 (2010). "MicroRNA-33 encoded by an intron of sterol regulatory element-binding binding protein 2 (Srebp2) regulates HDL in vivo."

Horton et al., The Journal of Clinical Investigation, 109(9):1125-1131 (2002). "SREBPs: activators of the complete program of cholesterol and fatty acid synthesis in the liver."

Kuhnert et al., Development, 135:3989-3993 (2008). "Attribution of vascular phenotypes of the murine Egfl7 locus to the microRNA miR-126."

Landgraf et al., Cell, 129:1401-1414 (2007). "A Mammalian microRNA Expression Atlas Based on Small RNA Library Sequencing."

Lewis et al., Cell, 115:787-798 (2003). "Prediction of Mammalian MicroRNA Targets."

Macron, Genomeweb, Sep. 3, 2009. "NIH Awards Nearly $6M in RNAi, miRNA Grants with Stimulus Money."

Marquart et al., PNAS, 107(27):12228-12232 with Supplemental Information (2010). "miR-33 links SREBP-2 induction to repression of sterol transporters."

Maxfield et al., Nature, 438:612-621 (2005). "Role of cholesterol and lipid organization in disease."

MiRNA Entry for MI0000091 "Stem-loop sequence has-mir 33a" accessed www.mirbase.org on Jan. 7, 2013.

Moore et al., Trends Endocrinol Metab, 21(12):699-706 Author Manuscript (2010). "microRNAs and cholesterol metabolism."

Muscat et al., The Journal of Biological Chemistry, 277(43):40722-40728 (2002). "Regulation of Cholesterol Homeostasis and Lipid Metabolism in Skeletal Muscle by Liver X Receptors."

Najafi-Shoushtari et al., Science, 328:1566-1569 (2010). "MicroRNA-33 and the SREBP Host Genes Cooperate to Control Cholesterol Homeostasis."

Obernosterer et al., RNA, 12:1161-1167 (2006). "Post-transcriptional regulation of microRNA expression."

Ozsolak et al., Genes Dev., 22:3172-3183 (2008). "Chromatin structure analyses identify miRNA promoters."

Parker et al., Nature, 428:754-758 (2004). "The endothelial-cell-derived secreted factor Egfl7 regulates vascular tube formation."

Ranalletta et al., Arterioscler Thromb Vasc Biol, 26:2308-2315 (2006). "Decreased Atherosclerosis in Low-Density Lipoprotein Receptor Knockout with Abcg1-/-Bone Marrow."

Rayner et al., Science, 328(5985):1570-1573 Author Manuscript (2010). "MiR-33 Contributes to the Regulation of Cholesterol Homeostasis."

Rayner et al., Nature, 478:404-409 (2011). "Inhibition of miR-33a/b in non-human primates raises plasma HDL and lowers VLDL triglycerides."

Rayner et al., The Journal of Clinical Investigation, 121(7):2921-2931 (2012). "Antagonism of miR-33 in mice promotes reverse cholesterol transport and regression of atherosclerosis."

Remaley et al., PNAS, 92(22):12685-12690 (1999). "Human ATP-binding cassette transporter 1 (ABC1): Genomic organization and identification of the genetic defect in the original Tangier disease kindred."

Rodriguez et al., Genome Res., 14:1902-1910 (2004). "Identification of Mammalian microRNA Host Genes and Transcription Units."

Sikand et al., Cancer Cell International, 9:21 (2009). "Intrinsic expression of host genes and intronic miRNAs in prostate carcinoma cells."

Simon et al., Cell, 133:903-915 (2008). "The MicroRNA miR-1 Regulates a MEF-2-Dependent Retrograde Signal at Neuromuscular Junctions."

Tagonov et al., PNAS, 103(33):12481-12486 (2006). "Nk-κB-dependent induction of microRNA miR-146, an inhibitor targeted to signaling proteins of innate immune responses."

Tall et al., Cell Metabolism, 7:365-375 (2008). "HDL, ABC Transporters, and Cholesterol Efflux: Implications for the Treatment of Atherosclerosis."

Tang et al., Genome Res., 18:104-112 (2008). "*Xenopus* microRNA genes are predominantly located within introns and are differentially expressed in adult frog tissues via post-transcriptional regulation."

TargetScan: Prediction of microRNA targets, Release 4.2, Apr. 2008. "Human ABCA1 3' UTR."

TargetScan: Prediction of microRNA targets, Release 4.2, Apr. 2008. "Human IRAK1 3' UTR."

TargetScan: Prediction of microRNA targets, Release 4.2, Apr. 2008. "Human TRAF6 3' UTR."

TargetScan: Prediction of microRNA targets, Release 4.2, Apr. 2008. "Predicted miRNA targets of miR-33."

TargetScan: Prediction of microRNA targets, Release 4.2, Apr. 2008. "Predicted miRNA targets of miR-122."

Assman, G. et al., Am. J. Cardiol, 77:1179-1184 (1996), "Hypertriglyceridemia and Elevated Lipoprotein(a) Are Risk Factors for Major Coronary Events in Middle-Aged Men".

Tang, X. et al, RNA, 15:287-293 (2009), "Identification of glucode-regulated miRNAs from pancreatic β cells reveals a role for miR-30d in insulin transcription".

Wilfred, B. et al., Molecular Genetics and Metabolism, 91:209-217 (2007), "Energizing miRNA research: A review of the role of miRNAs in lipid metabolism, with a prediction that miR-103/107 regulates human metabolic pathways".

Xie, Huangming, et al., Diabetes, 50:1050-1057 (2009), "MicroRNAs Induced During Adipogenesis that Accelerate Fat Cell Development Are Downregulated in Obesity".

\* cited by examiner

SEQ ID NO. 1 (Nucleotide sequence of miR-33 a):
      GUGCAUUGUAGUUGCAUUGCA

SEQ ID NO. 2 (Nucleotide sequence of miR-33 b):
      GUGCAUUGCUGUUGCAUUGC

SEQ ID NO. 3 (Anti-miR-33a oligonucleotide):
      UGCAAUGCAACUACAAUGCAC

SEQ ID NO. 4 (Anti-miR-33b oligonucleotide):
      GCAAUGCAACAGCAAUGCAC

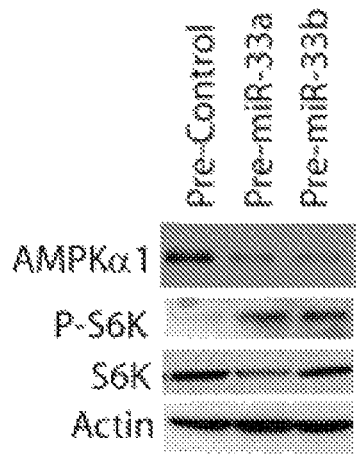
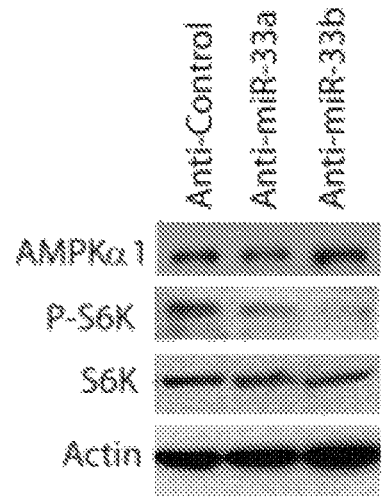
FIG. 5A　　　　FIG. 5B
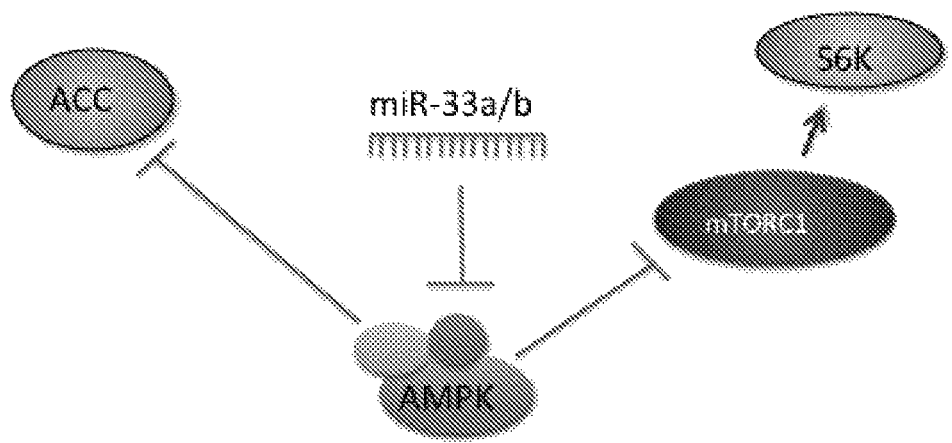
FIG. 5C

METHODS TARGETING MIR-33 MICRORNAS FOR REGULATING LIPID METABOLISM

CROSS REFERENCE TO RELATED APPLICATIONS CLAIM OF PRIORITY

This application is a 35 U.S.C. §371 National Stage Entry Application of International Application No. PCT/US2011/049207 filed Aug. 25, 2011, which designates the U.S., and which claims the benefit under 35 U.S.C. §119(e) of U.S. Provisional Patent Applications Ser. Nos. 61/377,077, filed on Aug. 25, 2010, and 61/387,284, filed on Sep. 28, 2010, the entire contents of which are hereby incorporated by reference. In addition, the entire contents of U.S. Application Ser. No. 61/165,041, filed on Mar. 31, 2009; and International Patent Application No. PCT/US2010/029376, filed on Mar. 31, 2010, are incorporated herein by reference.

FEDERALLY SPONSORED RESEARCH

This invention was made with government support under Grants No. R01GM071449 and R21DK084459 awarded by National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Aug. 23, 2011, is named 8-23-2011-Sequence Listing-60721036 and is 962 bytes in size.

BACKGROUND OF THE INVENTION

Abnormal cholesterol and lipid homeostasis are linked with prevalent diseases such as metabolic syndrome, atherosclerosis/cardiovascular disease, and type 2 diabetes. Cholesterol and lipids are trafficked in the blood as lipoprotein particles, such as low-density lipoprotein (LDL) and high-density lipoprotein (HDL) that ferry their fatty cargo to different cells and tissues. Excess circulating LDL can be oxidized and taken up by arterial macrophages, turning them into cholesterol/lipid-filled "foam cells" that are involved in the formation of atherosclerotic plaques. Triglycerides, as major components of very-low-density lipoprotein (VLDL), have been linked to atherosclerosis, and, by extension, the risk of heart disease and stroke. Elevated triglycerides (e.g., mildly elevated fasting levels, above 150 mg/dL (1.7 mmol/L), or high fasting levels above 200 mg/dL (2.26 mmol/L)) are common in subjects with metabolic syndrome/insulin resistance and those with poorly controlled diabetes, and contribute to the risk of atherosclerosis, heart disease, and stroke in that population. Increased stored triglycerides in tissues such as liver and white adipose tissue (WAT) are associated with non-alcoholic fatty liver disease and obesity, additional hallmarks of metabolic syndrome and insulin resistance.

SUMMARY OF THE INVENTION

As described herein, microRNAs 33a and 33b (miR-33a and 33b, also referred to herein as SEQ ID NOs. 1 and 2, respectively) regulate the expression of multiple proteins in humans and mice that coordinately control fatty acid/triglyceride/energy homeostasis. Thus the methods described herein can be used to counter the increase in circulating and stored triglyceride levels, and ameliorate non-alcoholic fatty liver disease and obesity and complications thereof (e.g., non-alcoholic steatohepatitis, hepatocellular carcinoma, type 2 diabetes, and atherosclerosis) associated with metabolic syndrome and insulin resistance.

In one aspect, the invention is directed to a method of reducing levels of serum triglycerides in a subject, the method comprising administering to the subject a therapeutically effective amount of an inhibitory nucleic acid that is complementary to SEQ ID NOs. 1 or 2 (e.g., complementary to a target region comprising the seed sequence of SEQ ID NOs. 1 or 2). In some embodiments, the methods include determining a level of triglycerides in the subject, and selecting the subject if they have (i.e., on the basis that they have) mildly elevated fasting levels (above 150 mg/dL (1.7 mmol/L)) or high fasting levels (above 200 mg/dL (2.26 mmol/L)).

In one embodiment, administration of the inhibitory nucleic acid that is complementary to SEQ ID NOs. 1 or 2 increases mitochondrial fatty acid beta-oxidation resulting in reduced levels of stored and circulating triglycerides.

In another embodiment, administration of the inhibitory nucleic acid that is complementary to SEQ ID NOs. 1 or 2 reduces insulin-dependent expression and function of SREBP-1c, thereby decreasing fatty acid and triglyceride production.

Also provided herein are methods for reducing obesity, or for treating or reducing the risk of developing type 2 diabetes, diabetic neuropathy, non-alcoholic fatty liver disease, non-alcoholic steatohepatitis, hepatocellular carcinoma, or cardiovascular disease in a subject, by administering to the subject a therapeutically effective amount of an inhibitory nucleic acid that is complementary to SEQ ID NOs. 1 or 2 (e.g., complementary to a target region comprising the seed sequence of SEQ ID NOs. 1 or 2).

In some embodiments, the subject has or is at risk of developing metabolic syndrome or Type 2 diabetes. In some embodiments, the method s include selecting a subject on the basis that they have or are at risk of developing metabolic syndrome or Type 2 diabetes.

In some embodiments, the methods include selecting a subject who is in need of weight loss. In some embodiments, the subject is selected if they have a BMI of 25 or above.

Unless otherwise defined, all technical and scientific terms used herein have the same meaning as commonly understood by one of ordinary skill in the art to which this invention belongs. In case of conflict, the present application, including definitions, will control.

As referred to herein, a "complementary nucleic acid sequence" is a nucleic acid sequence capable of hybridizing with another nucleic acid sequence comprised of complementary nucleotide base pairs. By "hybridize" is meant pair to form a double-stranded molecule between complementary nucleotide bases (e.g., adenine (A) forms a base pair with thymine (T), as does guanine (G) with cytosine (C) in DNA) under suitable conditions of stringency. (See, e.g., Wahl, G. M. and S. L. Berger (1987) Methods Enzymol. 152:399; Kimmel, A. R. (1987) Methods Enzymol. 152:507). For the purposes of the present invention, the inhibitory nucleic acid need not be complementary to the entire sequence, only enough of it to provide specific inhibition; for example in some embodiments the sequence is 100% complementary to at least nucleotides 2-7 of the miRNA ('seed sequence').

As used herein, an "antisense oligonucleotide" refers to a synthesized nucleic acid sequence that is complementary to a DNA or mRNA sequence, such as that of a microRNA.

"RNA" is a molecule comprising at least one or more ribonucleotide residues. A "ribonucleotide" is a nucleotide with a hydroxyl group at the 2' position of a beta-D-ribofuranose moiety. The term RNA, as used herein, includes double-stranded RNA, single-stranded RNA, isolated RNA, such as partially purified RNA, essentially pure RNA, synthetic RNA, recombinantly produced RNA, as well as altered RNA that differs from naturally occurring RNA by the addition, deletion, substitution and/or alteration of one or more nucleotides. Nucleotides of the RNA molecules can also comprise non-standard nucleotides, such as non-naturally occurring nucleotides or chemically synthesized nucleotides or deoxynucleotides.

A "microRNA" (miRNA) typically refers to a single-stranded RNA molecules of about 21-23 nucleotides in length, which regulates gene expression. miRNAs are encoded by genes from whose DNA they are transcribed but miRNAs are not translated into protein; instead each primary transcript is processed into a short stem-loop structure before undergoing further processing into a functional miRNA. Mature miRNA molecules are partially complementary to one or more messenger RNA (mRNA) molecules, and their main function is to down-regulate gene expression.

As used herein "an interfering RNA" refers to any double stranded or single stranded RNA sequence, capable—either directly or indirectly (i.e., upon conversion)—of inhibiting or down regulating gene expression by mediating RNA interference. Interfering RNA includes but is not limited to small interfering RNA ("siRNA") and small hairpin RNA ("shRNA"). "RNA interference" refers to the selective degradation of a sequence-compatible messenger RNA transcript.

As used herein "an shRNA" (small hairpin RNA) refers to an RNA molecule comprising an antisense region, a loop portion and a sense region, wherein the sense region has complementary nucleotides that base pair with the antisense region to form a duplex stem. Following post-transcriptional processing, the small hairpin RNA is converted into a small interfering RNA by a cleavage event mediated by the enzyme Dicer, which is a member of the RNase III family.

A "small interfering RNA" or "siRNA" as used herein refers to any small RNA molecule capable of inhibiting or down regulating gene expression by mediating RNA interference in a sequence specific manner. The small RNA can be, for example, about 18 to 21 nucleotides long.

As used herein, an "antagomir" refers to a small synthetic RNA having complementarity to a specific microRNA target, optionally with either mispairing at the cleavage site or one or more base modifications to inhibit cleavage.

As used herein, the phrase "post-transcriptional processing" refers to mRNA processing that occurs after transcription and is mediated, for example, by the enzymes Dicer and/or Drosha.

As used herein, the term "ABCA1" refers to the ATP-binding cassette, subfamily A, member 1, protein transporter, described, for example, by Remaley, A. T., *Proc. Nat. Acad. Sci.* 96: 12685-12690, 1999.

As used herein "an increase in ABCA1 protein expression" refers to an amount of ABCA1 protein that is at least about 1-fold more (for example 1, 2, 3, 4, 5, 10, 20, 30, 40, 50, 60, 70, 80, 90, 100, 1000, 10,000-fold or more) than the amount of ABCA1 protein in a subject prior to treatment according to the methods described herein. "Increased" as it refers to the amount of ABCA1 protein expression in a subject also means at least about 5% more (for example 5, 6, 7, 8, 9, 10, 15, 20, 25, 30, 35, 40, 45, 50, 55, 60, 65, 70, 75, 80, 85, 90, 95, 99 or 100%) than the amount of ABCA1 protein in the subject before treatment according to the methods described herein. Protein amounts can be measured according to methods known in the art.

By "an effective amount" is meant the amount of a required agent or composition comprising the agent to ameliorate the symptoms of a disease relative to an untreated patient. The effective amount of composition(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount."

As used herein, "cholesterol homeostasis" refers to the regulation of cholesterol uptake, cholesterol biosynthesis, cholesterol conversion to bile acids and excretion of bile acids as such processes occur in a subject having healthful levels of LDL, HDL and cholesterol in the blood (e.g., such healthful levels are also referred to herein as a "reference standard"). Accordingly, a subject in need of cholesterol homeostasis is in need of improved regulation resulting in a return to healthful levels of LDL, HDL and/or cholesterol in the blood.

A "subject" is a vertebrate, including any member of the class mammalia, including humans, domestic and farm animals, and zoo, sports or pet animals, such as mouse, rabbit, pig, sheep, goat, cattle and higher primates.

As used herein, a "vector" or "expression vector" is a nucleic acid-based delivery vehicle comprising regulatory sequences and a gene of interest, which can be used to transfer its contents into a cell.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Other definitions appear in context throughout this disclosure. Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

BRIEF DESCRIPTION OF THE DRAWINGS

FIG. 1B is a schematic illustration of proposed model for the role of AMPK in the regulation of lipid and glucose metabolism in skeletal muscle. AMPK activity may be increased by an altered energy nucleotide or by hormonal action. This activation of AMPK may result in an increase in glucose transport as well as an increase in fatty acid oxidation. AS160, Akt substrate of 160 kDa; Glut4, glucose transporter 4; PGC1a, PPARgamma co-activator 1a.

FIG. 2 lists the sequences of SEQ ID NO. 1 (Nucleotide sequence of miR-33 a); SEQ ID NO. 2 (Nucleotide sequence of miR-33 b); SEQ ID NO. 3 (Anti-miR-33a oligonucleotide); and SEQ ID NO. 4 (Anti-miR-33b oligonucleotide).

FIGS. 5A and 5B are Western blots showing that introduction of miR-33a/b precursors (5A) and antisense (5B) oligonucleotides into HepG2 cells results in increased and decreased mTOR signaling, respectively, as evidenced by changes in the levels of phosphorylation of the mTOR target S6 kinase monitored by a phospho-specific antibody (P-S6K). Total S6K levels are also shown for comparison.

FIG. 5C is a schematic illustration of a possible model, showing that introduction of excess miR-33b into HepG2 cells causes decreased AMPK phosphorylation (and inhibition) of the key downstream targets ACC and mTORC1.

DETAILED DESCRIPTION OF THE INVENTION

Figure 1A:
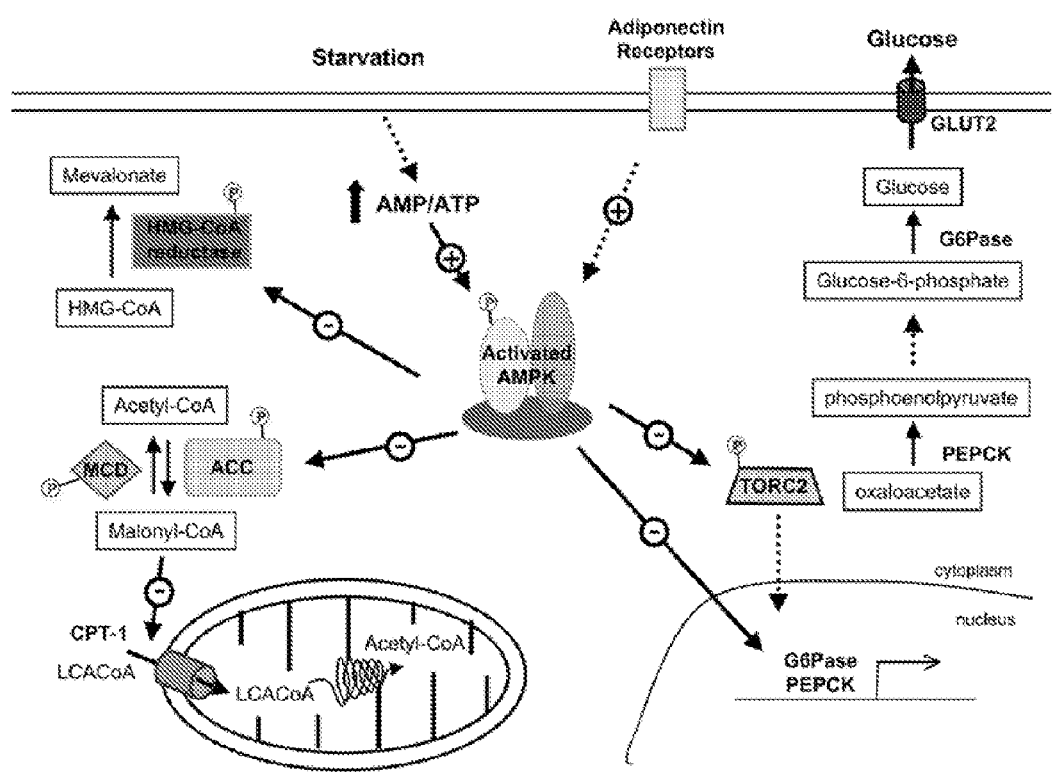
FIG. 1A is a schematic illustration of the role of AMPK in the regulation of hepatic metabolism. Activation of AMPK leads to the inhibition of cholesterol synthesis by the phosphorylation of HMG-CoA reductase. By inhibiting ACC and activating MCD, AMPK increases fatty acid oxidation via the regulation of malonyl CoA levels, which is both a critical precursor for biosynthesis of fatty acids and a potent inhibitor of CPT-1, the shuttle that controls the transfer of LCACoA into the mitochondria. AMPK inhibits hepatic glucose production via the phosphorylation of TORC2 and inhibition gene expression for key gluconeogenic enzymes, G6Pase and PEPCK, and for the transcriptional co-activator PGC-1a. ACC, acetyl-CoA carboxylase; AMPK, AMP-activated protein kinase; CPT1-a, carnitine palmitoyl transferase-1alpha; G6Pase, glucose-6-phosphatase; LCACoA, Long Chain acyl CoAs; MCD, malonyl-CoA decarboxylase; PEPCK, phosphoenolpyruvate carboxykinase; PGC1a, PPARgamma co-activator 1a; TORC2, transducer of regulated CREB activity 2.

The present invention is based, at least in part, on the discovery that microRNAs 33a and 33b (miR-33a and 33b, also referred to herein as SEQ ID NOs. 1 and 2, respectively) regulate the expression of multiple proteins in humans and mice that coordinately control fatty acid/triglyceride/energy homeostasis. Thus, miR-33a and/or b-targeting antisense-based therapeutic approaches can be used in humans for the treatment of metabolic syndrome-associated lipid abnormalities such as low HDL, elevated triglycerides, and obesity, or for treating or reducing the risk of developing type 2 diabetes, metabolic syndrome, diabetic neuropathy, non-alcoholic fatty liver disease, non-alcoholic steatohepatitis, hepatocellular carcinoma, or cardiovascular disease.

MicroRNAs (miRNAs) are a class of small (e.g., 18-24 nucleotides) non-coding RNAs that exist in a variety of organisms, including mammals, and are conserved in evolution. miRNAs are processed from hairpin precursors of about 70 nucleotides which are derived from primary transcripts through sequential cleavage by the RNAse III enzymes drosha and dicer. Many microRNAs can be encoded in intergenic regions, hosted within introns of pre-mRNAs or within ncRNA genes. Many miRNAs also tend to be clustered and transcribed as polycistrons and often have similar spatial temporal expression patterns. MiRNAs have been found to have roles in a variety of biological processes including developmental timing, differentiation, apoptosis, cell proliferation, organ development, and metabolism.

MicroRNAs-33 a and b (miR-33 a and b), referred to herein as SEQ ID NOs. 1 and 2, respectively, regulate the expression of multiple proteins in humans and mice that coordinately control fatty acid/triglyceride/energy homeostasis (Table 1). Accordingly, inhibition of miR-33 represents a novel therapeutic means to counter the increase in circulating and stored triglyceride levels, and ameliorate non-alcoholic fatty liver disease and obesity and complications thereof (e.g., non-alcoholic steatohepatitis, hepatocellular carcinoma, type 2 diabetes, and atherosclerosis) associated with metabolic syndrome and insulin resistance.

The methods described herein include the inhibition miR-33 a and/or b in a subject who has increased triglyceride levels, e.g., a subject who is insulin resistant and/or has the metabolic syndrome. This can be achieved, for example, by administering an inhibitory nucleic acid, e.g., an antisense oligonucleotide that is complementary to miR-33a or b, including but not limited to the oligonucleotides of SEQ ID NO. 3 or SEQ ID NO. 4. Other inhibitory nucleic acids for use in practicing the methods described herein and that are complementary to miR-33 a or b can be those which inhibit post-transcriptional processing of miR-33 a or b, such as an interfering RNA, including but not limited to an shRNA or siRNA, or an antagomir. In some embodiments, the inhibitory nucleic acid has a sequence as set forth in SEQ ID NO 2 in U.S. 61/511,562 ("TINY"); SEQ ID 4 in U.S. 61/511,565 or SEQ ID NO 27 in U.S. 61/511,564 (targeting miR-33b); or SEQ ID NO 30 in U.S. 61/511,565 or SEQ ID NO 4 in U.S. 61/511,564 (targeting miR-33a), all of which are incorporated herein by reference in their entirety.

Inhibitory Nucleic Acids

Inhibitory nucleic acids useful in the present methods and compositions include antisense oligonucleotides, ribozymes, external guide sequence (EGS) oligonucleotides, siRNA compounds, single- or double-stranded RNA interference (RNAi) compounds such as siRNA compounds, modified bases/locked nucleic acids (LNAs), antagomirs, peptide nucleic acids (PNAs), and other oligomeric compounds or oligonucleotide mimetics which hybridize to at least a portion of the target nucleic acid and modulate its function. In some embodiments, the inhibitory nucleic acids include antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs), or combinations thereof. See, e.g., WO 2010040112.

In some embodiments, the inhibitory nucleic acids are 10 to 50, 13 to 50, or 13 to 30 nucleotides in length. One having ordinary skill in the art will appreciate that this embodies oligonucleotides having antisense portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range therewithin. In some embodiments, the oligonucleotides are 15 nucleotides in length. In some embodiments, the antisense or oligonucleotide compounds of the invention are 12 or 13 to 30 nucleotides in length. One having ordinary skill in the art will appreciate that this embodies inhibitory nucleic acids having antisense portions of 12, 13, 14, 15, 16, 17, 18, 19, 20, 21, 22, 23, 24, 25, 26, 27, 28, 29 or 30 nucleotides in length, or any range therewithin.

In some embodiments, the inhibitory nucleic acids are chimeric oligonucleotides that contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. Chimeric inhibitory nucleic acids of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures comprise, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference.

In some embodiments, the inhibitory nucleic acid comprises at least one nucleotide modified at the 2' position of the sugar, most preferably a 2'-O-alkyl, 2'-O-alkyl-O-alkyl or 2'-fluoro-modified nucleotide. In other preferred embodiments, RNA modifications include 2'-fluoro, 2'-amino and 2' O-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than; 2'-deoxyoligonucleotides against a given target.

A number of nucleotide and nucleoside modifications have been shown to make the oligonucleotide into which they are incorporated more resistant to nuclease digestion than the native oligodeoxynucleotide; these modified oligos survive intact for a longer time than unmodified oligonucleotides. Specific examples of modified oligonucleotides include those comprising modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly CH2-NH—O—CH2, CH, ~N(CH3)~O~CH2 (known as a methylene(methylimino) or MMI backbone], CH2-O—N(CH3)-CH2, CH2-N(CH3)-N(CH3)-CH2 and O—N(CH3)-CH2-CH2 backbones, wherein the native phosphodiester backbone is represented as O—P—O—CH,); amide backbones (see De Mesmaeker et al. Ace. Chem. Res. 1995, 28:366-374); morpholino backbone structures (see Summerton and Weller, U.S. Pat. No. 5,034,506); peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone, see Nielsen et al., Science 1991, 254, 1497). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3' alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455, 233; 5,466,677; 5,476,925; 5,519,126; 5,536,821; 5,541,306; 5,550,111; 5,563, 253; 5,571,799; 5,587,361; and 5,625,050.

Morpholino-based oligomeric compounds are described in Dwaine A. Braasch and David R. Corey, Biochemistry, 2002, 41(14), 4503-4510); Genesis, volume 30, issue 3, 2001; Heasman, J., Dev. Biol., 2002, 243, 209-214; Nasevicius et al., Nat. Genet., 2000, 26, 216-220; Lacerra et al., Proc. Natl. Acad. Sci., 2000, 97, 9591-9596; and U.S. Pat. No. 5,034, 506, issued Jul. 23, 1991.

Cyclohexenyl nucleic acid oligonucleotide mimetics are described in Wang et al., J. Am. Chem. Soc., 2000, 122, 8595-8602.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts; see U.S. Pat. Nos.

5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

One or more substituted sugar moieties can also be included, e.g., one of the following at the 2' position: OH, SH, SCH$_3$, F, OCN, OCH$_3$OCH$_3$, OCH$_3$—O—(CH$_2$)n CH$_3$, O(CH$_2$)n NH$_2$ or O(CH$_2$)n CH$_3$ where n is from 1 to about 10; Ci to C10 lower alkyl, alkoxyalkoxy, substituted lower alkyl, alkaryl or aralkyl; Cl; Br; CN; CF3; OCF3; O—, S—, or N-alkyl; O—, S—, or N-alkenyl; SOCH3; SO2 CH3; ONO2; NO2; N3; NH2; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'-O-CH$_2$CH$_2$OCH$_3$, also known as 2'-O-(2-methoxyethyl)] (Martin et al, Helv. Chim. Acta, 1995, 78, 486). Other preferred modifications include 2'-methoxy (2'-0-CH$_3$), 2'-propoxy (2'-OCH$_2$CH$_2$CH$_3$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Inhibitory nucleic acids can also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine and 2,6-diaminopurine. Kornberg, A., DNA Replication, W.H. Freeman & Co., San Francisco, 1980, pp 75-77; Gebeyehu, G., et al. Nucl. Acids Res. 1987, 15:4513). A "universal" base known in the art, e.g., inosine, can also be included. 5-Me-C substitutions have been shown to increase nucleic acid duplex stability by 0.6-1.2<0>C. (Sanghvi, Y. S., in Crooke, S. T. and Lebleu, B., eds., Antisense Research and Applications, CRC Press, Boca Raton, 1993, pp. 276-278) and are presently preferred base substitutions.

It is not necessary for all positions in a given oligonucleotide to be uniformly modified, and in fact more than one of the aforementioned modifications may be incorporated in a single oligonucleotide or even at within a single nucleoside within an oligonucleotide.

In some embodiments, both a sugar and an internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative United States patents that teach the preparation of PNA compounds comprise, but are not limited to, U.S. Pat. Nos. 5,539, 082; 5,714,331; and 5,719,262, each of which is herein incorporated by reference. Further teaching of PNA compounds can be found in Nielsen et al, Science, 1991, 254, 1497-1500.

Inhibitory nucleic acids can also include one or more nucleobase (often referred to in the art simply as "base") modifications or substitutions. As used herein, "unmodified" or "natural" nucleobases comprise the purine bases adenine (A) and guanine (G), and the pyrimidine bases thymine (T), cytosine (C) and uracil (U). Modified nucleobases comprise other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleobases comprise those disclosed in U.S. Pat. No. 3,687,808, those disclosed in 'The Concise Encyclopedia of Polymer Science And Engineering', pages 858-859, Kroschwitz, J. I., ed. John Wiley & Sons, 1990, those disclosed by Englisch et al., Angewandle Chemie, International Edition', 1991, 30, page 613, and those disclosed by Sanghvi, Y. S., Chapter 15, Antisense Research and Applications', pages 289-302, Crooke, S. T. and Lebleu, B. ea., CRC Press, 1993. Certain of these nucleobases are particularly useful for increasing the binding affinity of the oligomeric compounds of the invention. These include 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2<0>C (Sanghvi, Y. S., Crooke, S. T. and Lebleu, B., eds, 'Antisense Research and Applications', CRC Press, Boca Raton, 1993, pp. 276-278) and are presently preferred base substitutions, even more particularly when combined with 2'-O-methoxyethyl sugar modifications. Modified nucleobases are described in U.S. Pat. No. 3,687,808, as well as U.S. Pat. Nos. 4,845,205; 5,130,302; 5,134,066; 5,175,273; 5,367, 066; 5,432,272; 5,457,187; 5,459,255; 5,484,908; 5,502,177; 5,525,711; 5,552,540; 5,587,469; 5,596,091; 5,614,617; 5,750,692, and 5,681,941, each of which is herein incorporated by reference.

In some embodiments, the inhibitory nucleic acids are chemically linked to one or more moieties or conjugates that enhance the activity, cellular distribution, or cellular uptake of the oligonucleotide. Such moieties comprise but are not limited to, lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S— tritylthiol (Manoharan et al, Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Mancharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-t oxycholesterol moiety (Crooke et al., J. Pharmacol. Exp. Ther., 1996, 277, 923-937). See also U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g., U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

The inhibitory nucleic acids useful in the present methods are sufficiently complementary to the target miRNA, i.e., hybridize sufficiently well and with sufficient specificity, to give the desired effect. "Complementary" refers to the capacity for pairing, through hydrogen bonding, between two sequences comprising naturally or non-naturally occurring bases or analogs thereof. For example, if a base at one position of an inhibitory nucleic acid is capable of hydrogen bonding with a base at the corresponding position of a miRNA, then the bases are considered to be complementary to each other at that position. In some embodiments, 100% complementarity is not required. In some embodiments, 100% complementarity is required.

Routine methods can be used to design an inhibitory nucleic acid that binds to the target sequence with sufficient specificity.

While the specific sequences of certain exemplary target segments are set forth herein, one of skill in the art will recognize that these serve to illustrate and describe particular embodiments within the scope of the present invention. Additional target segments are readily identifiable by one having ordinary skill in the art in view of this disclosure. Target segments of 5, 6, 7, 8, 9, 10 or more nucleotides in length comprising a stretch of at least five (5) consecutive nucleotides within the seed sequence, or immediately adjacent thereto, are considered to be suitable for targeting as well. In some embodiments, target segments can include sequences that comprise at least the 5 consecutive nucleotides from the 5'-terminus of one of the seed sequence (the remaining nucleotides being a consecutive stretch of the same RNA beginning immediately upstream of the 5'-terminus of the seed sequence and continuing until the inhibitory nucleic acid contains about 5 to about 30 nucleotides). In some embodiments, target segments are represented by RNA sequences that comprise at least the 5 consecutive nucleotides from the 3'-terminus of one of the seed sequence (the remaining nucleotides being a consecutive stretch of the same miRNA beginning immediately downstream of the 3'-terminus of the target segment and continuing until the inhibitory nucleic acid contains about 5 to about 30 nucleotides). One having skill in the art armed with the sequences provided herein will be able, without undue experimentation, to identify further preferred regions to target.

Once one or more target regions, segments or sites have been identified, inhibitory nucleic acid compounds are chosen that are sufficiently complementary to the target, i.e., that hybridize sufficiently well and with sufficient specificity (i.e., do not substantially bind to other non-target RNAs), to give the desired effect.

In the context of this invention, hybridization means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. Complementary, as used herein, refers to the capacity for precise pairing between two nucleotides. For example, if a nucleotide at a certain position of an oligonucleotide is capable of hydrogen bonding with a nucleotide at the same position of a miRNA molecule, then the inhibitory nucleic acid and the miRNA are considered to be complementary to each other at that position. The inhibitory nucleic acids and the miRNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the inhibitory nucleic acid and the miRNA target.

For example, if a base at one position of an inhibitory nucleic acid is capable of hydrogen bonding with a base at the corresponding position of a miRNA, then the bases are considered to be complementary to each other at that position. 100% complementarity is not required.

It is understood in the art that a complementary nucleic acid sequence need not be 100% complementary to that of its target nucleic acid to be specifically hybridisable. A complementary nucleic acid sequence for purposes of the present methods is specifically hybridisable when binding of the sequence to the target miRNA molecule interferes with the normal function of the target miRNA to cause a loss of activity, and there is a sufficient degree of complementarity to avoid non-specific binding of the sequence to non-target miRNA sequences under conditions in which specific binding is desired, e.g., under physiological conditions in the case of in vivo assays or therapeutic treatment, and in the case of in vitro assays, under conditions in which the assays are performed under suitable conditions of stringency. For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., *Molecular Cloning: A Laboratory Manual*, Cold Spring Harbor Laboratory Press, New York.

In general, the inhibitory nucleic acids useful in the methods described herein have at least 80% sequence complementarity to a target region within the target nucleic acid, e.g., 90%, 95%, or 100% sequence complementarity to the target region within an miRNA. For example, an antisense compound in which 18 of 20 nucleobases of the antisense oligonucleotide are complementary, and would therefore specifically hybridize, to a target region would represent 90 percent complementarity. Percent complementarity of an inhibitory nucleic acid with a region of a target nucleic acid can be determined routinely using basic local alignment search tools (BLAST programs) (Altschul et al., J. Mol. Biol., 1990, 215, 403-410; Zhang and Madden, Genome Res., 1997, 7, 649-656). Antisense and other compounds of the invention that hybridize to an miRNA are identified through routine experimentation. In general the inhibitory nucleic acids must retain specificity for their target, i.e., must not directly bind to, or directly significantly affect expression levels of, transcripts other than the intended target.

For further disclosure regarding inhibitory nucleic acids, please see US2010/0317718 (antisense oligos); US2010/0249052 (double-stranded ribonucleic acid (dsRNA)); US2009/0181914 and US2010/0234451 (LNAs); US2007/0191294 (siRNA analogues); US2008/0249039 (modified siRNA); and WO2010/129746 and WO2010/040112 (inhibitory nucleic acids).

Antisense

Antisense oligonucleotides are typically designed to block expression of a DNA or RNA target by binding to the target and halting expression at the level of transcription, translation, or splicing. Antisense oligonucleotides of the present invention are complementary nucleic acid sequences designed to hybridize under stringent conditions to miR-33 a and/or b. Thus, oligonucleotides are chosen that are sufficiently complementary to the target, i.e., that hybridize sufficiently well and with sufficient specificity, to give the desired effect.

Modified Bases/Locked Nucleic Acids (LNAs)

In some embodiments, the inhibitory nucleic acids used in the methods described herein comprise one or more modified bonds or bases. Modified bases include phosphorothioate, methylphosphonate, peptide nucleic acids, or locked nucleic acid (LNA) molecules. Preferably, the modified nucleotides are locked nucleic acid molecules, including [alpha]-L-LNAs. LNAs comprise ribonucleic acid analogues wherein the ribose ring is "locked" by a methylene bridge between the 2'-oxygen and the 4'-carbon—i.e., oligonucleotides containing at least one LNA monomer, that is, one 2'-O,4'-C-methylene-β-D-ribofuranosyl nucleotide. LNA bases form standard Watson-Crick base pairs but the locked configuration increases the rate and stability of the basepairing reaction (Jepsen et al., Oligonucleotides, 14, 130-146 (2004)). LNAs also have increased affinity to base pair with RNA as compared to DNA. These properties render LNAs especially useful as probes for fluorescence in situ hybridization (FISH) and comparative genomic hybridization, as knockdown tools for miRNAs, and as antisense oligonucleotides to target mRNAs or other RNAs, e.g., miRNAs as described herien.

The LNA molecules can include molecules comprising 10-30, e.g., 12-24, e.g., 12, 13, 14, 15, 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the miRNA. The LNA molecules can be chemically synthesized using methods known in the art.

The LNA molecules can be designed using any method known in the art; a number of algorithms are known, and are commercially available (e.g., on the internet, for example at exiqon.com). See, e.g., You et al., Nuc. Acids. Res. 34:e60 (2006); McTigue et al., Biochemistry 43:5388-405 (2004); and Levin et al., Nuc. Acids. Res. 34:e142 (2006). For example, "gene walk" methods, similar to those used to design antisense oligos, can be used to optimize the inhibitory activity of the LNA; for example, a series of oligonucleotides of 10-30 nucleotides spanning the length of a target miRNA can be prepared, followed by testing for activity. Optionally, gaps, e.g., of 5-10 nucleotides or more, can be left between the LNAs to reduce the number of oligonucleotides synthesized and tested. GC content is preferably between about 30-60%. General guidelines for designing LNAs are known in the art; for example, LNA sequences will bind very tightly to other LNA sequences, so it is preferable to avoid significant complementarity within an LNA. Contiguous runs of three or more Gs or Cs, or more than four LNA residues, should be avoided where possible (for example, it may not be possible with very short (e.g., about 9-10 nt) oligonucleotides). In some embodiments, the LNAs are xylo-LNAs.

In some embodiments, the LNA molecules can be designed to target a specific region of the miRNA. For example, a specific functional region can be targeted, e.g., a region comprising a seed sequence. Alternatively or in addition, highly conserved regions can be targeted, e.g., regions identified by aligning sequences from disparate species such as primate (e.g., human) and rodent (e.g., mouse) and looking for regions with high degrees of identity. Percent identity can be determined routinely using basic local alignment search tools (BLAST programs) (Altschul et al., J. Mol. Biol., 1990, 215, 403-410; Zhang and Madden, Genome Res., 1997, 7, 649-656), e.g., using the default parameters.

For additional information regarding LNAs see U.S. Pat. Nos. 6,268,490; 6,734,291; 6,770,748; 6,794,499; 7,034,133; 7,053,207; 7,060,809; 7,084,125; and 7,572,582; and U.S. Pre-Grant Pub. Nos. 20100267018; 20100261175; and 20100035968; Koshkin et al. Tetrahedron 54, 3607-3630 (1998); Obika et al. Tetrahedron Lett. 39, 5401-5404 (1998); Jepsen et al., Oligonucleotides 14:130-146 (2004); Kauppinen et al., Drug Disc. Today 2(3):287-290 (2005); and Ponting et al., Cell 136(4):629-641 (2009), and references cited therein.

See also U.S. Ser. No. 61/412,862, which is incorporated by reference herein in its entirety.

Antagomirs

In some embodiments, the antisense is an antagomir. Antagomirs are chemically modified antisense oligonucleotides that target a microRNA. For example, an antagomir for use in the methods described herein can include a nucleotide sequence sufficiently complementary to hybridize to a miRNA target sequence of about 12 to 25 nucleotides, preferably about 15 to 23 nucleotides.

In general, antagomirs include a cholesterol moiety, e.g., at the 3'-end. In some embodiments, antagomirs have various modifications for RNase protection and pharmacologic properties such as enhanced tissue and cellular uptake. For example, In addition to the modifications discussed above for antisense oligos, an antagomir can have one or more of complete or partial 2'-O-methylation of sugar and/or a phosphorothioate backbone. Phosphorothioate modifications provide protection against RNase activity and their lipophilicity contributes to enhanced tissue uptake. In some embodiments, the antagomir cam include six phosphorothioate backbone modifications; two phosphorothioates are located at the 5'-end and four at the 3'-end. See, e.g., Krutzfeldt et al., Nature 438, 685-689 (2005); Czech, N Engl J Med 2006; 354:1194-1195 (2006); Robertson et al., Silence. 1:10 (2010); Marquez and McCaffrey, Hum Gene Ther. 19(1):27-38 (2008); van Rooij et al., Circ Res. 103(9):919-928 (2008); and Liu et al., Int. J. Mol. Sci. 9:978-999 (2008).

Antagomirs useful in the present methods can also be modified with respect to their length or otherwise the number of nucleotides making up the antagomir. In general, the antagomirs are about 20-21 nucleotides in length for optimal function, as this size matches the size of the mature microRNAs for miR-33a and b. The antagomirs must retain specificity for their target, i.e., must not directly bind to, or directly significantly affect expression levels of, transcripts other than the intended target.

In some embodiments, the inhibitory nucleic acid is locked and includes a cholesterol moiety (e.g., a locked antagomir).

siRNA

In some embodiments, the nucleic acid sequence that is complementary to SEQ ID NOs. 1 or 2 can be an interfering RNA, including but not limited to a small interfering RNA ("siRNA") or a small hairpin RNA ("shRNA"). Methods for constructing interfering RNAs are well known in the art. For example, the interfering RNA can be assembled from two separate oligonucleotides, where one strand is the sense strand and the other is the antisense strand, wherein the antisense and sense strands are self-complementary (i.e., each strand comprises nucleotide sequence that is complementary to nucleotide sequence in the other strand; such as where the antisense strand and sense strand form a duplex or double stranded structure); the antisense strand comprises nucleotide sequence that is complementary to a nucleotide sequence in a target nucleic acid molecule or a portion thereof (i.e., an undesired gene) and the sense strand comprises nucleotide sequence corresponding to the target nucleic acid sequence or a portion thereof. Alternatively, interfering RNA is assembled from a single oligonucleotide, where the self-complementary sense and antisense regions are linked by means of nucleic acid based or non-nucleic acid-based linker(s). The interfering RNA can be a polynucleotide with a duplex, asymmetric duplex, hairpin or asymmetric hairpin secondary structure, having self-complementary sense and antisense regions, wherein the antisense region comprises a nucleotide sequence that is complementary to nucleotide sequence in a separate target nucleic acid molecule or a portion thereof and the sense region having nucleotide sequence corresponding to the target nucleic acid sequence or a portion thereof. The interfering can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNA interference.

In some embodiments, the interfering RNA coding region encodes a self-complementary RNA molecule having a sense region, an antisense region and a loop region. Such an RNA molecule when expressed desirably forms a "hairpin" structure, and is referred to herein as an "shRNA." The loop region is generally between about 2 and about 10 nucleotides in length. In some embodiments, the loop region is from about 6 to about 9 nucleotides in length. In some embodiments, the sense region and the antisense region are between about 15 and about 20 nucleotides in length. Following post-transcriptional processing, the small hairpin RNA is converted into a siRNA by a cleavage event mediated by the enzyme Dicer, which is a member of the RNase III family. The siRNA is then capable of inhibiting the expression of a gene with which it shares homology. For details, see Brummelkamp et al., Science 296:550-553, (2002); Lee et al, Nature Biotechnol., 20, 500-505, (2002); Miyagishi and Taira, Nature Biotechnol 20:497-500, (2002); Paddison et al. Genes & Dev. 16:948-958, (2002); Paul, Nature Biotechnol, 20, 505-508, (2002); Sui, Proc. Natl. Acad. Sd. USA, 99(6), 5515-5520, (2002); Yu et al. Proc Natl Acad Sci USA 99:6047-6052, (2002).

The target RNA cleavage reaction guided by siRNAs is highly sequence specific. In general, siRNA containing a nucleotide sequences identical to a portion of the target nucleic acid (i.e., a target region comprising the seed sequence of miR-33 a and/or b) are preferred for inhibition. However, 100% sequence identity between the siRNA and the target gene is not required to practice the present invention. Thus the invention has the advantage of being able to tolerate sequence variations that might be expected due to genetic mutation, strain polymorphism, or evolutionary divergence. For example, siRNA sequences with insertions, deletions, and single point mutations relative to the target sequence have also been found to be effective for inhibition. Alternatively, siRNA sequences with nucleotide analog substitutions or insertions can be effective for inhibition. In general the siRNAs must retain specificity for their target, i.e., must not directly bind to, or directly significantly affect expression levels of, transcripts other than the intended target.

Ribozymes

Trans-cleaving enzymatic nucleic acid molecules can also be used; they have shown promise as therapeutic agents for human disease (Usman & McSwiggen, 1995 Ann. Rep. Med. Chem. 30, 285-294; Christoffersen and Marr, 1995 J. Med. Chem. 38, 2023-2037). Enzymatic nucleic acid molecules can be designed to cleave specific miRNA targets within the background of cellular RNA. Such a cleavage event renders the miRNA non-functional.

In general, enzymatic nucleic acids with RNA cleaving activity act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base pairing, and once bound to the correct site, acts enzymatically to cut the target RNA. Strategic cleavage of such a target RNA will destroy its activity. After an enzymatic nucleic acid has bound and cleaved its RNA target, it is released from that RNA to search for another target and can repeatedly bind and cleave new targets.

Several approaches such as in vitro selection (evolution) strategies (Orgel, 1979, Proc. R. Soc. London, B 205, 435) have been used to evolve new nucleic acid catalysts capable of catalyzing a variety of reactions, such as cleavage and ligation of phosphodiester linkages and amide linkages, (Joyce, 1989, Gene, 82, 83-87; Beaudry et al., 1992, Science 257, 635-641; Joyce, 1992, Scientific American 267, 90-97; Breaker et al, 1994, TIBTECH 12, 268; Bartel et al, 1993, Science 261: 1411-1418; Szostak, 1993, TIBS 17, 89-93; Kumar et al, 1995, FASEB J., 9, 1183; Breaker, 1996, Curr. Op. Biotech., 1, 442). The development of ribozymes that are optimal for catalytic activity would contribute significantly to any strategy that employs RNA-cleaving ribozymes for the purpose of regulating gene expression. The hammerhead ribozyme, for example, functions with a catalytic rate (kcat) of about 1 $min^{-1}$ in the presence of saturating (10 mM) concentrations of $Mg^{2+}$ cofactor. An artificial "RNA ligase" ribozyme has been shown to catalyze the corresponding self-modification reaction with a rate of about 100 $min^{-1}$. In addition, it is known that certain modified hammerhead ribozymes that have substrate binding arms made of DNA catalyze RNA cleavage with multiple turn-over rates that approach 100 $min^{-1}$.

Making and Using Inhibitory Nucleic Acids

The nucleic acid sequences used to practice the methods described herein, whether RNA, cDNA, genomic DNA, vectors, viruses or hybrids thereof, can be isolated from a variety of sources, genetically engineered, amplified, and/or expressed/generated recombinantly. Recombinant nucleic acid sequences can be individually isolated or cloned and tested for a desired activity. Any recombinant expression system can be used, including e.g. in vitro, bacterial, fungal, mammalian, yeast, insect or plant cell expression systems.

Nucleic acid sequences of the invention can be inserted into delivery vectors and expressed from transcription units within the vectors. The recombinant vectors can be DNA plasmids or viral vectors. Generation of the vector construct can be accomplished using any suitable genetic engineering techniques well known in the art, including, without limitation, the standard techniques of PCR, oligonucleotide synthesis, restriction endonuclease digestion, ligation, transformation, plasmid purification, and DNA sequencing, for example as described in Sambrook et al. Molecular Cloning: A Laboratory Manual. (1989)), Coffin et al. (Retroviruses. (1997)) and "RNA Viruses: A Practical Approach" (Alan J. Cann, Ed., Oxford University Press, (2000)). As will be apparent to one of ordinary skill in the art, a variety of suitable vectors are available for transferring nucleic acids of the invention into cells. The selection of an appropriate vector to deliver nucleic acids and optimization of the conditions for insertion of the selected expression vector into the cell, are within the scope of one of ordinary skill in the art without the need for undue experimentation. Viral vectors comprise a nucleotide sequence having sequences for the production of recombinant virus in a packaging cell. Viral vectors expressing nucleic acids of the invention can be constructed based on viral backbones including, but not limited to, a retrovirus, lentivirus, adenovirus, adeno-associated virus, pox virus or alphavirus. The recombinant vectors capable of expressing the nucleic acids of the invention can be delivered as described herein, and persist in target cells (e.g., stable transformants).

Nucleic acid sequences used to practice this invention can be synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066. Nucleic acid sequences of the invention can be stabilized against nucleolytic degradation such as by the incorporation of a modification, e.g., a nucleotide modification. For example, nucleic acid sequences of the invention includes a phosphorothioate at least the first, second, or third internucleotide linkage at the 5' or 3' end of the nucleotide sequence. As another example, the nucleic acid sequence can include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-β-DMAP), 2'-O-dimethylaminoethyloxyethyl (2'-O-DMAEOE), or 2'-O—N-methylacetamido (2'-O—NMA). As another example, the nucleic acid sequence can include at least one 2'-O-methyl-modified nucleotide, and in some embodiments, all of the nucleotides include a 2'-O-methyl modification. In some embodiments, the nucleic acids are "locked," i.e., comprise nucleic acid analogues in which the ribose ring is "locked" by a methylene bridge connecting the 2'-O atom and the 4'-C atom (see, e.g., Kaupinnen et al., Drug Disc. Today 2(3):287-290 (2005); Koshkin et al., J. Am. Chem. Soc., 120(50):13252-13253 (1998)). For additional modifications see US 20100004320, US 20090298916, and US 20090143326.

Techniques for the manipulation of nucleic acids used to practice this invention, such as, e.g., subcloning, labeling probes (e.g., random-primer labeling using Klenow polymerase, nick translation, amplification), sequencing, hybridization and the like are well described in the scientific and patent literature, see, e.g., Sambrook et al., *Molecular Cloning; A Laboratory Manual* 3d ed. (2001); *Current Protocols in Molecular Biology*, Ausubel et al., eds. (John Wiley & Sons, Inc., New York 2010); Kriegler, *Gene Transfer and Expression: A Laboratory Manual* (1990); *Laboratory Techniques In Biochemistry And Molecular Biology: Hybridization With Nucleic Acid Probes, Part I. Theory and Nucleic Acid Preparation*, Tijssen, ed. Elsevier, N.Y. (1993).

Pharmaceutical Compositions

The methods described herein can include the administration of pharmaceutical compositions and formulations comprising inhibitory nucleic acid sequences designed to target miR33 a/b.

In some embodiments, the compositions are formulated with a pharmaceutically acceptable carrier. The pharmaceutical compositions and formulations can be administered parenterally, topically, orally or by local administration, such as by aerosol or transdermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration of pharmaceuticals are well described in the scientific and patent literature, see, e.g., *Remington: The Science and Practice of Pharmacy*, 21st ed., 2005.

The inhibitory nucleic acids can be administered alone or as a component of a pharmaceutical formulation (composition). The compounds may be formulated for administration, in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the compositions of the invention include those suitable for intradermal, inhalation, oral/nasal, topical, parenteral, rectal, and/or intravaginal administration. The formulations may conveniently be presented in unit dosage form and may be prepared by any methods well known in the art of pharmacy. The amount of active ingredient (e.g., nucleic acid sequences of this invention) which can be combined with a carrier material to produce a single dosage form will vary depending upon the host being treated, the particular mode of administration, e.g., intradermal or inhalation. The amount of active ingredient which can be combined with a carrier material to produce a single dosage form will generally be that amount of the compound which produces a therapeutic effect, e.g., an antigen specific T cell or humoral response.

Pharmaceutical formulations of this invention can be prepared according to any method known to the art for the manufacture of pharmaceuticals. Such drugs can contain sweetening agents, flavoring agents, coloring agents and preserving agents. A formulation can be admixtured with non-toxic pharmaceutically acceptable excipients which are suitable for manufacture. Formulations may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, on patches, in implants, etc.

Pharmaceutical formulations for oral administration can be formulated using pharmaceutically acceptable carriers well known in the art in appropriate and suitable dosages. Such carriers enable the pharmaceuticals to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxy-methylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate. Push-fit capsules can contain active agents mixed with a filler or binders such as lactose or starches, lubricants such as talc or magnesium stearate, and, optionally, stabilizers. In soft capsules, the active agents can be dissolved or suspended in suitable liquids, such as fatty oils, liquid paraffin, or liquid polyethylene glycol with or without stabilizers.

Aqueous suspensions can contain an active agent (e.g., nucleic acid sequences of the invention) in admixture with excipients suitable for the manufacture of aqueous suspensions, e.g., for aqueous intradermal injections. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

In some embodiments, oil-based pharmaceuticals are used for administration of nucleic acid sequences of the invention. Oil-based suspensions can be formulated by suspending an active agent in a vegetable oil, such as arachis oil, olive oil, sesame oil or coconut oil, or in a mineral oil such as liquid paraffin; or a mixture of these. See e.g., U.S. Pat. No. 5,716, 928 describing using essential oils or essential oil components for increasing bioavailability and reducing inter- and intra-individual variability of orally administered hydrophobic pharmaceutical compounds (see also U.S. Pat. No. 5,858, 401). The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto (1997) J. Pharmacol. Exp. Ther. 281:93-102.

Pharmaceutical formulations can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent. In alternative embodiments, these injectable oil-in-water emulsions of the invention comprise a paraffin oil, a sorbitan monooleate, an ethoxylated sorbitan monooleate and/or an ethoxylated sorbitan trioleate.

The pharmaceutical compounds can also be administered by in intranasal, intraocular and intravaginal routes including suppositories, insufflation, powders and aerosol formulations (for examples of steroid inhalants, see e.g., Rohatagi (1995) J. Clin. Pharmacol. 35:1187-1193; Tjwa (1995) Ann. Allergy Asthma Immunol. 75:107-111). Suppositories formulations can be prepared by mixing the drug with a suitable non-irritating excipient which is solid at ordinary temperatures but liquid at body temperatures and will therefore melt in the body to release the drug. Such materials are cocoa butter and polyethylene glycols.

In some embodiments, the pharmaceutical compounds can be delivered transdermally, by a topical route, formulated as applicator sticks, solutions, suspensions, emulsions, gels, creams, ointments, pastes, jellies, paints, powders, and aerosols.

In some embodiments, the pharmaceutical compounds can also be delivered as microspheres for slow release in the body. For example, microspheres can be administered via intradermal injection of drug which slowly release subcutaneously; see Rao (1995) J. Biomater. Sci. Polym. Ed. 7:623-645; as biodegradable and injectable gel formulations, see, e.g., Gao (1995) Pharm. Res. 12:857-863 (1995); or, as microspheres for oral administration, see, e.g., Eyles (1997) J. Pharm. Pharmacol. 49:669-674.

In some embodiments, the pharmaceutical compounds can be parenterally administered, such as by intravenous (IV) administration or administration into a body cavity or lumen of an organ. These formulations can comprise a solution of active agent dissolved in a pharmaceutically acceptable carrier. Acceptable vehicles and solvents that can be employed are water and Ringer's solution, an isotonic sodium chloride. In addition, sterile fixed oils can be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated using those suitable dispersing or wetting agents and suspending agents. The sterile injectable preparation can also be a suspension in a nontoxic parenterally-acceptable diluent or solvent, such as a solution of 1,3-butanediol. The administration can be by bolus or continuous infusion (e.g., substantially uninterrupted introduction into a blood vessel for a specified period of time).

In some embodiments, the pharmaceutical compounds and formulations can be lyophilized. Stable lyophilized formulations comprising an inhibitory nucleic acid can be made by lyophilizing a solution comprising a pharmaceutical of the invention and a bulking agent, e.g., mannitol, trehalose, raffinose, and sucrose or mixtures thereof. A process for preparing a stable lyophilized formulation can include lyophilizing a solution about 2.5 mg/mL protein, about 15 mg/mL sucrose, about 19 mg/mL NaCl, and a sodium citrate buffer having a pH greater than 5.5 but less than 6.5. See, e.g., U.S. 20040028670.

The compositions and formulations can be delivered by the use of liposomes. By using liposomes, particularly where the liposome surface carries ligands specific for target cells, or are otherwise preferentially directed to a specific organ, one can focus the delivery of the active agent into target cells in vivo. See, e.g., U.S. Pat. Nos. 6,063,400; 6,007,839; Al-Muhammed (1996) J. Microencapsul. 13:293-306; Chonn (1995) Curr. Opin. Biotechnol. 6:698-708; Ostro (1989) Am. J. Hosp. Pharm. 46:1576-1587.

The formulations of the invention can be administered for prophylactic and/or therapeutic treatments. In some embodiments, for therapeutic applications, compositions are administered to a subject who is need of reduced triglyceride levels, or who is at risk of or has a disorder described herein, in an amount sufficient to cure, alleviate or partially arrest the clinical manifestations of the disorder or its complications; this can be called a therapeutically effective amount. For example, in some embodiments, pharmaceutical compositions of the invention are administered in an amount sufficient to decrease serum levels of triglycerides in the subject.

The amount of pharmaceutical composition adequate to accomplish this is a therapeutically effective dose. The dosage schedule and amounts effective for this use, i.e., the dosing regimen, will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; Remington: The Science and Practice of Pharmacy, 21st ed., 2005). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods of the invention are correct and appropriate.

Single or multiple administrations of formulations can be given depending on for example: the dosage and frequency as required and tolerated by the patient, the degree and amount of cholesterol homeostasis generated after each administration, and the like. The formulations should provide a sufficient quantity of active agent to effectively treat, prevent or ameliorate conditions, diseases or symptoms, e.g., increase the expression of ABCA1, increase efflux of intracellular cholesterol and/or production of HDL in the liver and/or decrease the amount of cholesterol circulating the blood of a subject in need of cholesterol homeostasis.

In alternative embodiments, pharmaceutical formulations for oral administration are in a daily amount of between about 1 to 100 or more mg per kilogram of body weight per day. Lower dosages can be used, in contrast to administration orally, into the blood stream, into a body cavity or into a lumen of an organ. Substantially higher dosages can be used in topical or oral administration or administering by powders, spray or inhalation. Actual methods for preparing parenterally or non-parenterally administrable formulations will be known or apparent to those skilled in the art and are described in more detail in such publications as Remington: The Science and Practice of Pharmacy, 21st ed., 2005.

Various studies have reported successful mammalian dosing using complementary nucleic acid sequences. For example, Esau C., et al., (2006) Cell Metabolism, 3(2):87-98 reported dosing of normal mice with intraperitoneal doses of miR-122 antisense oligonucleotide ranging from 12.5 to 75 mg/kg twice weekly for 4 weeks. The mice appeared healthy and normal at the end of treatment, with no loss of body weight or reduced food intake. Plasma transaminase levels were in the normal range (AST ¾ 45, ALT ¾ 35) for all doses with the exception of the 75 mg/kg dose of miR-122 ASO, which showed a very mild increase in ALT and AST levels. They concluded that 50 mg/kg was an effective, non-toxic dose. Another study by Krützfeldt J., et al., (2005) Nature 438, 685-689, injected anatgomirs to silence miR-122 in mice using a total dose of 80, 160 or 240 mg per kg body weight. The highest dose resulted in a complete loss of miR-122 signal. In yet another study, locked nucleic acids ("LNAs") were successfully applied in primates to silence miR-122. Elmen J., et al., (2008) Nature 452, 896-899, report that efficient silencing of miR-122 was achieved in primates by three doses of 10 mg kg-1 LNA-antimiR, leading to a long-lasting and reversible decrease in total plasma cholesterol without any evidence for LNA-associated toxicities or histopathological changes in the study animals.

In some embodiments, the methods described herein can include co-administration with other drugs or pharmaceuticals, e.g., compositions for providing cholesterol homeostasis. For example, the inhibitory nucleic acids can be co-administered with drugs for treating or reducing risk of a disorder described herein.

Elevated Triglycerides

Triglyceride (triacylglycerol, TAG or triacylglyceride) is an ester derived from glycerol and three fatty acids, and is the main constituent of vegetable oil and animal fats (Nelson, D. L.; Cox, M. M. Lehninger, Principles of Biochemistry. 3rd Ed. Worth Publishing: New York, 2000).

The American Heart Association has set guidelines for triglyceride levels (after fasting for 8-12 hours), as follows:

| Level (mg/dL) | Level (mmol/L) | Interpretation |
|---|---|---|
| <150 | <1.69 | Normal range, low risk |
| 150-199 | 1.70-2.25 | Borderline high |
| 200-499 | 2.26-5.65 | High |
| >500 | >5.65 | Very high: high risk |

Fasting triglyceride levels can be determined using any means known in the art, e.g., enzymatically using a glycerol kinase reaction-based colorimetric assay.

Diabetic and Pre-Diabetic Subjects

In some embodiments, the subjects treated by the methods described herein have diabetes, i.e., are diabetic. A person who is diabetic has one or more of a Fasting Plasma Glucose Test result of 126 mg/dL or more; a 2-Hour Plasma Glucose Result in a Oral Glucose Tolerance Test of 200 mg/dL or more; and blood glucose level of 200 mg/dL or above. In some embodiments, the subjects treated by the methods described herein are being treated for diabetes, e.g., have been prescribed or are taking insulin, meglitinides, biguanides, thiazolidinediones, or alpha-glucosidase inhibitors.

In some embodiments the subjects are pre-diabetic, e.g., they have impaired glucose tolerance or impaired fasting glucose, e.g., as determined by standard clinical methods such as the intravenous glucose tolerance test (IVGTT) or oral glucose tolerance test (OGTT), e.g., a value of 7.8-11.0 mmol/L two hours after a 75 g glucose drink for impaired glucose tolerance, or a fasting glucose level (e.g., before breakfast) of 6.1-6.9 mmol/L.

The pathogenesis of type 2 diabetes is believed to generally involve two core defects: insulin resistance and β-cell failure (Martin et al., Lancet 340:925-929 (1992); Weyer et al., J. Clin. Invest. 104:787-794 (1999); DeFronzo et al., Diabetes Care. 15:318-368 (1992)). Important advances towards the understanding of the development of peripheral insulin resistance have been made in both animal models and humans (Bruning et al., Cell 88:561-572 (1997); Lauro et al., Nat. Genet. 20:294-298 (1998); Nandi et al., Physiol. Rev. 84:623-647 (2004); Sreekumar et al., Diabetes 51:1913-1920 (2002); McCarthy and Froguel, Am. J. Physiol. Endocrinol. Metab. 283:E217-E225 (2002); Mauvais-Jarvis and Kahn, Diabetes. Metab. 26:433-448 (2000); Petersen et al., N. Engl. J. Med. 350:664-671 (2004)). Thus, those subjects who have or are at risk for insulin resistance or impaired glucose tolerance are readily identifiable, and the treatment goals are well defined.

In some embodiments, the methods described herein include selecting subjects who have diabetes or pre-diabetes. In some embodiments, the following table is used to identify and/or select subjects who are diabetic or have pre-diabetes, i.e., impaired glucose tolerance and/or impaired fasting glucose.

| Fasting Blood Glucose | |
|---|---|
| From 70 to 99 mg/dL (3.9 to 5.5 mmol/L) | Normal fasting glucose |
| From 100 to 125 mg/dL (5.6 to 6.9 mmol/L) | Impaired fasting glucose (pre-diabetes) |
| 126 mg/dL (7.0 mmol/L) and above on more than one testing occasion | Diabetes |
| Oral Glucose Tolerance Test (OGTT) [except pregnancy] (2 hours after a 75-gram glucose drink) | |
| Less than 140 mg/dL (7.8 mmol/L) | Normal glucose tolerance |
| From 140 to 200 mg/dL (7.8 to 11.1 mmol/L) | Impaired glucose tolerance (pre-diabetes) |
| Over 200 mg/dL (11.1 mmol/L) on more than one testing occasion | Diabetes |

Body Mass Index (BMI)

Obesity increases a subject's risk of developing T2D. BMI is determined by weight relative to height, and equals a person's weight in kilograms divided by height in meters squared (BMI=kg/m$^2$). Accepted interpretations are given in Table 2.

TABLE 2

| Category | BMI |
|---|---|
| Underweight | ≥18.5 |
| Normal weight | 18.5-24.9 |
| Overweight | 25-29.9 |
| Obese | ≤30 |

Thus, the methods described herein can include determining a subject's height, determining a subject's weight, and calculating BMI from the values determined thereby. Alternatively, the methods described herein can include reviewing a subject's medical history to determine their BMI.

In some embodiments, the methods described herein include selecting subjects who have a BMI of 30 or above (i.e., obese subjects).

Metabolic Syndrome

In some embodiments, the methods include determining whether a subject has the metabolic syndrome, and selecting the subject if they do have the metabolic syndrome, then administering an inhibitory nucleic acid as described herein. Determining whether a subject has the metabolic syndrome can include reviewing their medical history, or ordering or performing such tests as are necessary to establish a diagnosis.

The metabolic syndrome, initially termed Syndrome X (Reaven, Diabetes. 37(12):1595-1607 (1988)), refers to a clustering of obesity, dyslipidemia, non-alcoholic fatty liver disease, hypertension, and insulin resistance. All components of the metabolic syndrome are traditional risk factors for vascular disease. As used herein, the metabolic syndrome is defined by the presence of at least 3 of the following: abdominal obesity (excessive fat tissue in and around the abdomen, as measured by waist circumference: e.g., greater than 40 inches for men, and greater than 35 inches for women), fasting blood triglycerides (e.g., greater than or equal to 150 mg/dL), low blood HDL (e.g., less than 40 mg/dL for men, and less than 50 mg/dL for women), high blood pressure (e.g., greater than or equal to 130/85 mmHg) and/or elevated fasting glucose (e.g., greater than or equal to 110 mg/dL). In some embodiments, levels of these criteria may be higher or lower, depending on the subject; for example, in subjects of Asian ancestry; see, e.g., Meigs, Curr. Op. Endocrin. Diabetes, 13(2):103-110 (2006). A determination of the presence of metabolic syndrome can be made, e.g., by reviewing the subject's medical history, or by reviewing test results.

Based on data from the Third National Health and Nutrition Examination Survey (NHANES III) approximately 24% of the adults in the United States qualify as having the metabolic syndrome (Ford et al., JAMA. 287(3):356-359 (2002)). Insulin resistance is now felt to be central in the pathogenesis of these related disorders.

Non-alcoholic fatty liver disease (NAFLD) and its most severe form, non-alcoholic steatohepatitis (NASH), are associated with high fat diet, high triglyceride levels, obesity, the metabolic syndrome and type II diabetes, and pose an increased risk of cardiovascular disease. NAFLD is an accumulation of fat in the liver that is not a result of excessive consumption of alcohol. 15% to 25% of cases of NAFLD progress and are associated with inflammation and liver damage; this condition is referred to as NASH. NASH is associated with an increased risk of developing liver cirrhosis and subsequence complications, including hepatocellular carcinoma. A diagnosis of NAFLD or NASH can be made by methods known in the art, e.g., by histological examination of liver biopsy samples.

EXAMPLES

The invention is further described in the following examples, which do not limit the scope of the invention described in the claims.

Example 1

Predicted Targets of miR-33 in Humans and Mice

The cholesterol/lipid transporter ABCA1 is targeted by miR-33, resulting in decreased cholesterol efflux from macrophages and lowered HDL levels in mice. See, e.g., Najafi-Shoushtari et al., Science. 328(5985):1566-9 (2010); Marquart et al., Proc Natl Acad Sci USA. 107(27):12228-32 (2010); and Rayner et al., Science. 328(5985):1570-3 (2010).

Further bioinformatics analysis employing the TargetScan and miRbase microRNA target prediction websites indicate that miR-33a/b also regulate the expression of multiple proteins in humans and mice that coordinately control fatty acid/triglyceride/energy homeostasis (Table 1).

TABLE 1

Predicted targets of miR-33a/b involved in fatty acid/triglyceride/energy homeostasis

| Gene | Function |
|---|---|
| ABCA1 | Cholesterol transport |
| CROT | Fatty acid beta-oxidation |
| AMPK (alpha1 catalytic subunit) | Energy homeostasis |
| MRPS25 | mitochondrial ribosomal protein S25 |
| MRPL49 | mitochondrial ribosomal protein L49 |
| HADHB | mitochondrial beta-oxidation of long chain fatty acids |
| IRS2 | Knock-down of IRS-2 in mouse liver causes upregulation of SREBP-1c and expression of lipogenic enzymes, and accumulation of lipids in liver |

TABLE 1-continued

Predicted targets of miR-33a/b involved in fatty acid/triglyceride/ energy homeostasis

| Gene | Function |
| --- | --- |
| SIK1 | Salt-inducible Kinase Regulates Hepatic Lipogenesis by Controlling SREBP- 1c Phosphorylation. Yoon et al. J. Biol. Chem. 2009 284: 10446-10452 |
| Citrate Synthase | Krebs Cycle, Inhibited by high ATP/ADP ratio, high Acetyl-CoA/CoA ratio, high NADH/NAD ratio (associated with abundant Energy) |
| Cpt1a | Fatty acid beta-oxidation |
| PPARalpha | Fatty acid beta-oxidation |
| PGC1alpha | Fatty acid beta-oxidation |
| SIRT6 | Liver glucose and triglyceride homeostasis |

Figures 1B, 2:
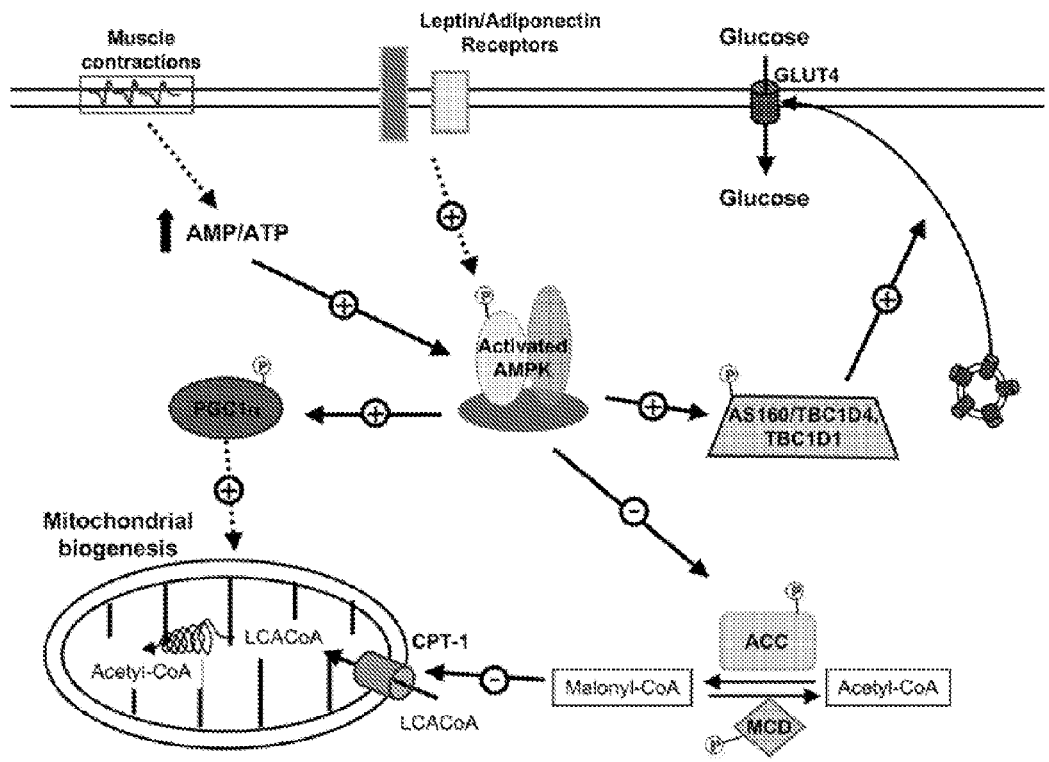

For example, Carnitine O-octanoyltransferase (CROT) converts 4,8-dimethylnonanoyl-CoA to its corresponding carnitine ester. This transesterification occurs in the peroxisome and is necessary for transport of medium- and long-chain acyl-CoA molecules out of the peroxisome to the cytosol and mitochondria. The protein thus plays a role in lipid metabolism and fatty acid beta-oxidation. Another predicted miR-33a/b target, Hydroxyacyl-Coenzyme A dehydrogenase/3-ketoacyl-Coenzyme A thiolase/enoyl-Coenzyme A hydratase beta (HADHB), encodes a subunit of the mitochondrial tri-functional protein, which catalyzes the last three steps of mitochondrial beta-oxidation of long chain fatty acids. The CPT1A gene encodes a liver enzyme termed carnitine palmitoyl transferase I, which assists in the transport of long-chain fatty acids into mitochondria (FIGS. 1A-B). This process is necessary for these fats to be broken down for energy. Long-chain fatty acids must be joined to carnitine for entry into the mitochondria. Carnitine palmitoyl transferase I connects the long-chain fatty acids to carnitine to promote this transport process. CPT1A is inhibited by malonyl-CoA, the product of the lipogenic enzyme acetyl-CoA carboxylase (ACC).

AMP kinase (AMPK) is an enzyme that plays a key role in cellular energy homeostasis (FIGS. 1A-B), directing cellular responses to low nutrient intake, stimulating hepatic fatty acid beta-oxidation and ketogenesis while limiting cholesterol and TAG synthesis (Hardie et al., Biochem. Soc. Trans. 39(1):1-13 (2011)). Lipogenesis is also blocked by direct phosphorylation and inhibition of acetyl-CoA carboxylase (ACC) by AMPK. In addition, AMPK promotes conservation of cellular energy stores by inhibiting the mTOR signaling pathway, and by downregulating gluconeogenesis and glucose export from the liver. AMPK is stimulated by fasting and inhibited by high ratios of ATP:AMP. The net effect of AMPK activation is stimulation of hepatic fatty acid oxidation and ketogenesis, inhibition of cholesterol synthesis, lipogenesis, and triglyceride synthesis, inhibition of adipocyte lipolysis and lipogenesis, stimulation of skeletal muscle fatty acid oxidation and muscle glucose uptake, and modulation of insulin secretion by pancreatic beta-cells. AMPK also inhibits ACC by direct phosphorylation, resulting in down-regulation of fatty acid biosynthesis (FIG. 1A).

Citrate synthase (CS) is an enzyme in the Krebs Cycle that produces citrate. The enzyme is inhibited by high ratios of ATP:ADP, acetyl-CoA:CoA, and NADH:NAD, as high concentrations of ATP, acetyl-CoA, and NADH show that the energy supply is high for the cell. Two mitochondrial ribosomal proteins (MRPS25 and MRPL49) are also predicted miR-33a/b targets. The nuclear receptor PPARalpha controls the expression of genes involved in fatty acid beta-oxidation and is a major regulator of energy homeostasis. PGC1alpha is a PPARalpha co-activator that also promotes mitochondrial biogenesis and which is stimulated by AMPK (FIG. 1B).

SIRT6 is an $NAD^+$-dependent histone deacetylase that has been shown to control glucose homeostasis by regulating glycolytic genes and glucose uptake (see, e.g., Kim et al., Cell Metab 12(3):224-236 (2010); Xiao et al., J Biol Chem 285 (47):36776-36784 (2010)), as well as controlling hepatic lipogenesis and triglyceride homeostasis (see, e.g., Kim et al., Cell Metab 12(3):224-236 (2010)). SIRT6 modulates the acetylation state of histone H3 lysine 9 (H3K9Ac) and histone H3 lysine 56 (H3K56Ac) at genomic/chromatin targets (Michishita et al., Nature 452(7186):492-496 (2008); Michishita et al., Cell Cycle 8(16):2664-2666 (2009); Yang et al., Cell Cycle 8(16):2662-2663 (2009)). SIRT6 has also been shown to control genes regulated by the hypoxia-responsive transcription factor HIF1a (Zhong et al., Cell 140(2):280-293 (2010)). SIRT6 directly regulates several lipogenic SREBP target genes (e.g., FASN, SCD-1, ELOVL6) at the chromatin/transcription-level in mouse liver (Kim et al., Cell Metab 12(3):224-236 (2010)), suggesting that it might also negatively regulate SREBP-1-dependent hepatic lipogenesis.

Down-regulation of all of these proteins together by miR-33a/b is expected to lead to decreased mitochondrial fatty acid beta-oxidation, and result in elevated stored and circulating triglycerides.

Multiple predicted miR-33a/b targets affect the expression and function of SREBP-1c, the host gene for miR-33b. For example, insulin receptor substrate 2 (IRS2) is a cytoplasmic signaling molecule that mediates effects of insulin. IRS2 is phosphorylated by the insulin receptor tyrosine kinase upon receptor stimulation. Expression of the lipogenic SREBP-1c gene is upregulated in response to insulin signaling. Chronic hyperinsulinemia down-regulates the mRNA for IRS2, an essential component of the insulin-signaling pathway in liver, thereby producing insulin resistance. Despite IRS2 deficiency, insulin continues to stimulate production of SREBP-1c, a transcription factor that activates fatty acid synthesis. Moreover, knockdown of IRS2 in mouse liver causes upregulation of SREBP-1c and expression of lipogenic enzymes, and accumulation of lipids in liver. This is thought to result from increased insulin signaling through IRS1. Salt-inducible kinase 1 (SIK1) is an SNF1-like kinase that has been shown to down-regulate hepatic lipogenesis by controlling SREBP-1c phosphorylation. AMPK and SIK1 function together down-stream of the LKB1 kinase complex in response to energy stress to modulate metabolic processes. Targeting of IRS2 and SIK1 by miR-33a/b is predicted to result in upregulation of insulin-dependent expression and function of SREBP-1c, causing increased fatty acid and triglyceride production due to elevated expression of SREBP-1c target genes involved in lipogenesis (e.g., by recruiting the CBP/p300 and ARC/Mediator co-activators to activate cholesterogenic and lipogenic target genes see, e.g., Näär et al. Genes Dev 12(19):3020-3031 (1998); Näär et al. Nature 398 (6730):828-832 (1999); Näär et al. Genes Dev 16(11):1339-1344 (2002); Taatjes et al. Science 295(5557):1058-1062 (2002); Yang et al. Nature 442(7103):700-704 (2006); and Walker et al. Genes Dev 24(13):1403-1417 (2010)). Moreover, co-expression of miR-33b with the SREBP-1c host gene in response to increased insulin signaling due to IRS2 down-regulation is expected to further enforce this pathway in a feed-forward manner.

Taken together, the bioinformatics analysis suggests that miR-33b and the SREBP-1c host gene coordinately control a network of metabolic regulators to promote increased lipid production and storage and decreased mitochondrial lipid degradation and energy consumption. This inter-connected regulatory circuit is likely to be highly active in insulin-resistant individuals and is predicted to significantly contribute to the elevated triglycerides and obesity that are hallmarks of metabolic syndrome and risk factors for cardiovascular disease and type 2 diabetes.

Antisense therapeutics targeting miR-33b (and, possibly, miR-33a) are expected to reverse the down-regulation of the targets shown in Table 1 and not only increase HDL, but also ameliorate increased circulating triglycerides and liver and adipose fat storage that are cardinal features of metabolic syndrome and insulin resistance.

Example 2

Modulation of miR-33a/b Affects the Activity of AMP Kinase (AMPK) and Fatty Acid Beta-Oxidation Enzymes The effect of modulating levels of miR-33a/b on several of the predicted targets listed in Table 1, including AMPK, CROT, HADHB, Cpt1a, SIK1, Citrate Synthase, IRS2, and SIRT6, was evaluated. In addition, the effect of Pre-miR-33a and b on phosphorylation of downstream AMPK targets, including acetyl-CoA carboxylase (ACC) and AMPK alpha 1, was investigated. HepG2 cells were cultured in MEM with 10% FBS, supplemented with glutamine and sodium pyruvate and in the presence of antibiotics. Pre-microRNA duplex and Anti-miRs for mir-33a and mir-33b and controls were obtained from Ambion (Applied Biosystems) (Pre-miR-33a: GUGCAUUGUAGUUGCAUUGCA (SEQ ID NO:1) Pre-miR-33b: GUGCAUUGCUGUUGCAUUGC (SEQ ID NO:2), Anti-miR-33a: UGCAAUGCAACUACAAUGCAC (SEQ ID NO:3), Anti-miR-33b: GCAAUGCAACAG-CAAUGCAC (SEQ ID NO:4). Pre-miRs are double-stranded RNA, whereas Anti-miRs are single-stranded RNA).

Transfections were carried out using the Amaxa Cell Line Nucleofector Kit V (Lonza) at a final concentration of 50 nM. Cells were plated at low density (30-40%). After 8 hours, cells were serum starved for 42 hours to synchronize them, transfected and subsequently plated at high density. The effect of Anti-miRs and Pre-miRs were evaluated 24-48 hrs post-transfection. Immunoblotting was carried out according to standard procedures. Antibodies were procured from Abcam (AMPK ab89214, CPT1A ab53532, CROT ab57405, HADHB ab88256, IRS2 ab52606, SIK1 ab64428, citrate synthase ab96600 and SIRT6 ab62739) Cell Signaling (ACC 3676, P-ACC 3661, P-AMPK 2535), and Sigma (actin, A4700).

Figure 3A:
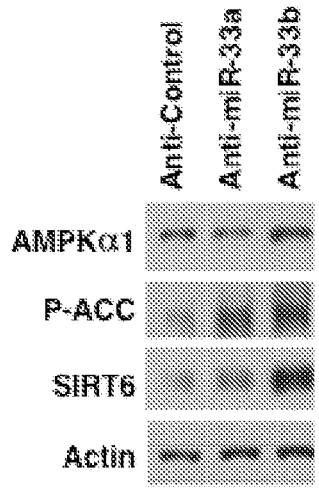
FIG. 3A is a Western blot showing that miR-33a and b antisense oligonucleotides transfected into human HepG2 liver cells cause increased levels of AMPK alpha 1, with a concomitant increase in the phosphorylation of its substrate acetyl CoA carboxylase (ACC) by a phospho-specific antibody (P-ACC). There is also an increase in the levels of the NAD+-dependent histone deacetylase SIRT6.
Figure 3B:
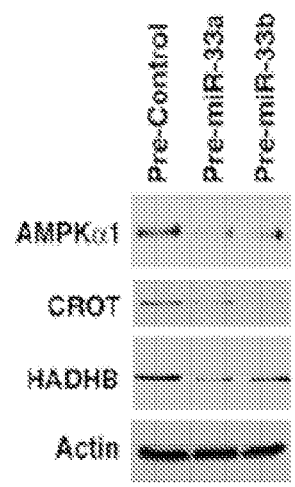
FIG. 3B is a Western blot showing that introduction of miR-33b precursor oligonucleotides into HepG2 cells results in decreased levels of AMPK alpha 1 with a concomitant decrease in the phosphorylation of its substrate acetyl CoA carboxylase (ACC) by a phospho-specific antibody (P-ACC). There is also a strong decrease in the levels of SIRT6.
Figure 3C:
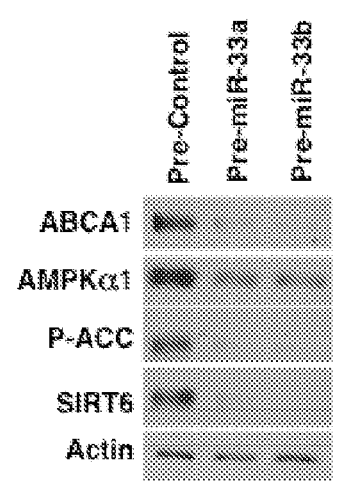
FIG. 3C is a Western blot showing that transfection of miR-33a and b precursor oligonucleotides into HepG2 cells results in decreased levels of AMPK alpha 1, as well as the fatty acid beta-oxidation enzymes CROT and HADHB
Figure 4A:
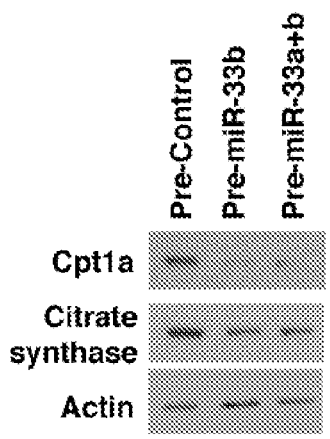
FIG. 4A is a Western blot showing that miR-33a and b antisense oligonucleotides transfected into human HepG2 liver cells cause decreased levels of Cpt1a and citrate synthase.
Figure 4B:
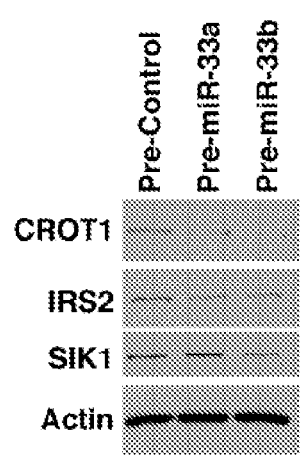
FIG. 4B is a Western blot showing that transfection of miR-33a and b precursor oligonucleotides into HepG2 cells results in decreased levels of CROT, IRS2, SIK1, and SIRT6.
Figure 4C:
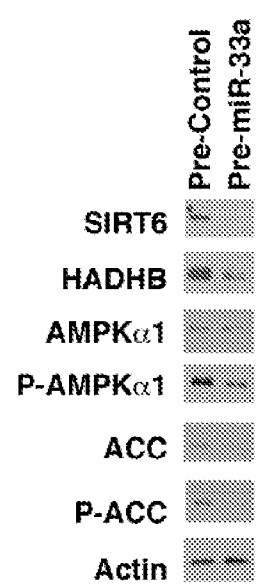
FIG. 4C is a Western blot showing that introduction of miR-33a precursor oligonucleotides into HepG2 cells results in decreased levels of SIRT6, HADHB, AMPK alpha 1 with a concomitant decrease in the phosphorylation of its substrate acetyl CoA carboxylase (ACC) by a phospho-specific antibody (P-ACC).

The results indicate that miR-33a and b antisense oligonucleotides transfected into human HepG2 liver cells cause increased levels of AMPK alpha 1, phosphorylated ACC (P-ACC), and SIRT6 (See FIG. 3A). Transfection of miR-33a and b precursor oligonucleotides into HepG2 cells results in decreased levels of AMPK alpha 1, the fatty acid beta-oxidation enzymes CROT, HADHB, and Cpt1a, citrate synthase, IRS2, SIK1, and SIRT6 (see FIGS. 3B, C, 4A-C). Introduction of miR-33a and b precursor oligonucleotides into HepG2 cells results in decreased levels of AMPK alpha 1 with a concomitant decrease in the phosphorylation of its substrates acetyl-CoA carboxylase (ACC) and AMPK alpha 1 itself by phospho-specific antibodies (P-ACC and P-AMPKalpha1) (see FIGS. 3B and 4C). Moreover, treatment of HepG2 cells with miR-33a and b precursor and antisense oligonucleotides results in changes in the phosphorylation status of the mTOR signaling target S6 kinase (S6K), as judged by a phospho-specific antibody (see FIG. 5A,B).

These data demonstrate that miR-33a/b regulate the AMPK alpha 1 subunit and the fatty acid beta-oxidation genes CROT and HADHB in HepG2 liver cells, and that introduction of excess miR-33b into HepG2 cells causes decreased AMPK phosphorylation (and inhibition) of the key downstream targets ACC and mTORC1 (FIGS. 1A-B and 2, and FIG. 5C). Because of the central role of ACC in fatty acid biosynthesis, and the essential role for the ACC enzymatic product Malonyl-CoA in inhibition of CPT-I and fatty acid beta-oxidation, it is expected that miR-33b antisense therapeutics will result in increased AMPK-dependent phosphorylation of ACC and decreased synthesis of fatty acid and Malonyl-CoA, causing increased fatty acid beta-oxidation. This is expected to decrease adipose and liver triglyceride storage, as well as circulating triglycerides.

Figures 6A, 6B:
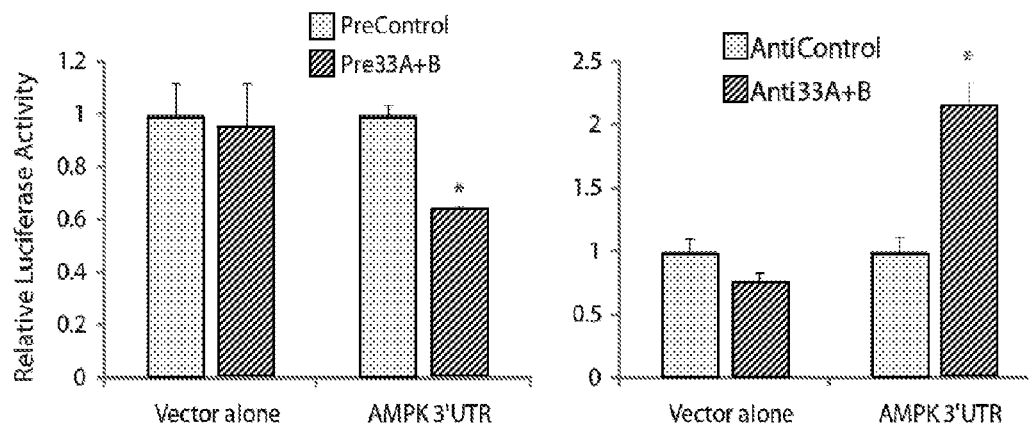
FIGS. 6A and 6B are bar graphs showing the results of co-transfection with either miR-33a/b precursors (6A) or miR-33a/b antisense oligonucleotides on Luciferase expression of an AMPK 3'UTR-Luciferase reporter construct.

To establish that miR-33a/b acts through the AMPK alpha 1 3'UTR, miR-33a/b effects on an AMPKa1 3'UTR-Luciferase reporter were analyzed. The data provides support for direct regulation of the AMPKa1 3'UTR by miR-33a/b (FIGS. 6A-B).

Figure 7:
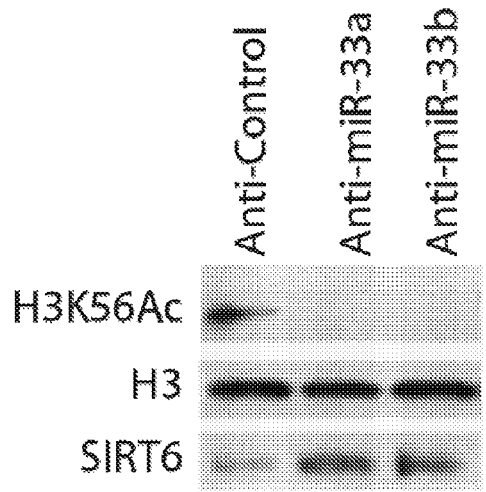
FIG. 7 is a Western blot showing a specific effect of anti-miR-33a/b on expression levels of H3K56Ac, a target of SIRT6.

Given the physiological importance of SIRT6 in hepatic and systemic glucose and triglyceride homeostasis, the effects of miR-33a/b on SIRT6-regulated processes, such as histone H3K9 and H3K56 acetylation, were also studied. As shown in FIG. 7, SIRT6-dependent deacetylation of histone H3 lysine 56 (H3K56Ac) is regulated by miR-33a/b in HepG2 cells.

While LNA-antisense targeting of miR-33a in mice resulted in significantly elevated circulating HDL, effects on circulating triglycerides was not observed in this model. This may be because, unlike humans, mice have naturally high levels of circulating HDL, and, as discussed above, mice lack miR-33b in the SREBP-1 gene.

Example 3 mir-33a/b and Insulin Signaling

Hepatic SREBP-1c expression is strongly increased in response to insulin signaling and in patients with insulin resistance/metabolic syndrome (Horton et al., J Clin Invest 109(9):1125-1131 (2002); Repa et al., Genes Dev 14(22): 2819-2830 (2000); Biddinger et al., Cell Metab 7(2):125-134 (2008); Muller-Wieland and Kotzka, Ann N Y Acad Sci 967: 19-27 (2002)). miR-33b expression would be expected to be co-elevated with the SREBP-1 host gene upon insulin treatment. This insulin-dependent increase of miR-33b expression would then be expected to lead to decreased levels of its predicted targets, such as ABCA1, AMPK, SIRT6, and fatty acid beta-oxidation enzymes in human liver cells.

To test this hypothesis, HepG2 human hepatoma cells were cultured under standard cell culture conditions in MEM medium (supplemented with 10% fetal bovine serum, L-Glutamine (2 mM), Penicillin (50 units/ml) Streptomycin (50 ug/ml) and Sodium Pyruvate (1 mM)). Cells were grown at low cell density (30-40%), trypsinized and seeded into wells of a 6-well plate pretreated with poly-lysine. After 24 hours, insulin (was added to a final concentration of 10 nM or 100 nM. At the indicated time-points (0 hours, 4 hours) the cells were harvested and RNA isolated with Trizol (Invitrogen) or the miRVana miRNA isolation kit (Ambion, Invitrogen).

QRT-PCR for SREBP genes (SREBF1 and SREBF2) and SREBP targets (SCD1 and LDLR) was normalized to 18S control and the 0 hours timepoint. MicroRNAs were quantified using the TaqMan microRNA assay kit for hsa-miR- 33a/b (Applied Biosystems), with U6 RNA used as an internal control. Error bars are standard deviation of pipetting replicates.

Figure 8A:
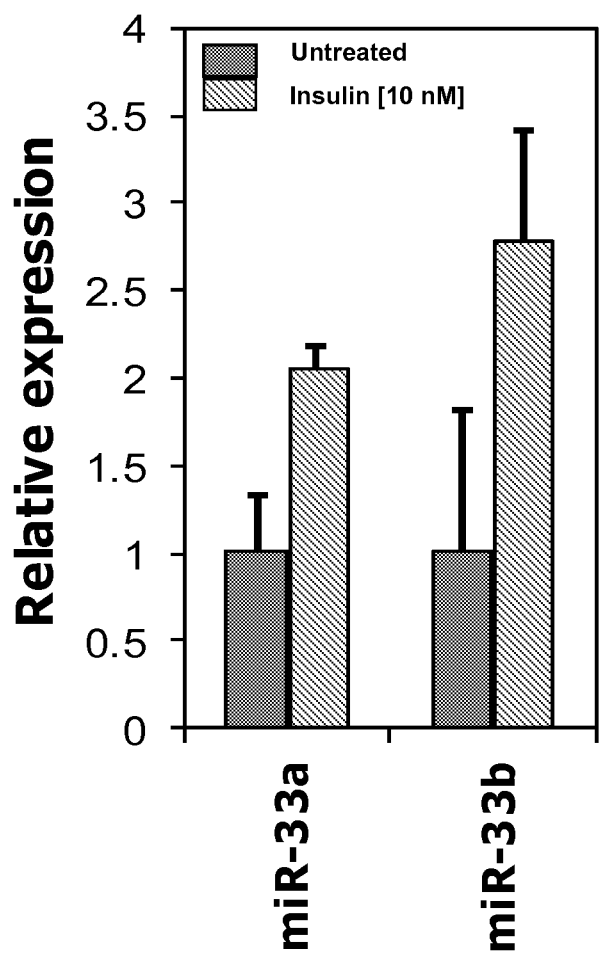
FIG. 8A is a bar graph showing the effect of insulin treatment on levels of miR-33a and b.
Figure 8B:
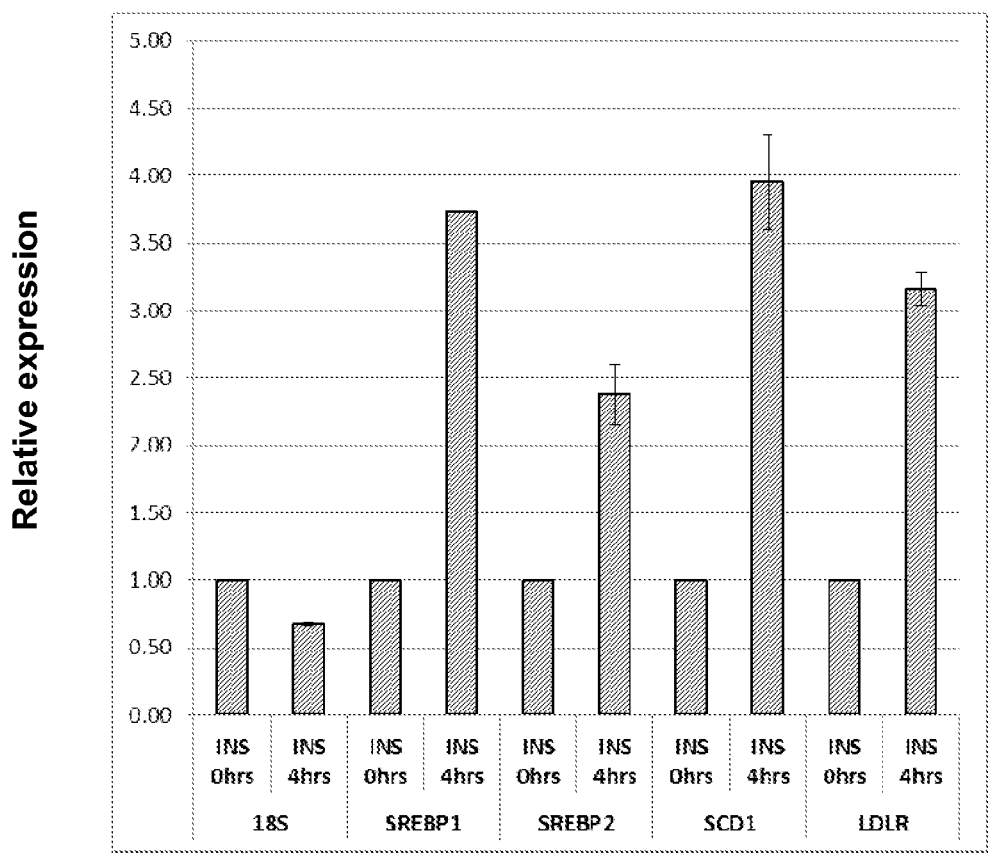
FIG. 8B is a bar graph showing the effects of insulin treatment on levels of the indicated SREBP genes and SREBP downstream targets.

The results, shown in FIG. 8A, demonstrated the expected elevation in miR-33a/b, with a somewhat greater increase in miR-33b. As shown in FIG. 8B, insulin treatment also increased levels of the SREBP genes and targets.

Example 4

MiR-33a/b Antisense Treatment In Vivo

The efficacy and safety of using miR-33a/b-targeting LNA-antisense oligonucleotides to change of metabolic profiles is evaluated in African green monkeys sustained on a high-fat/cholesterol diet as previously described (Elmen et al., Nature 452(7189):896-899 (2008); Lanford et al., Science 327(5962):198-201 (2010)).

Captive female African Green monkeys, 4-10 years old and in the approximate weight range of 3-5.5 kg, are employed in the study. Two blood samples are collected from each pre-screened animal over the subsequent 7-day period for plasma cholesterol levels, including total cholesterol, VLDL, LDL and HDL to produce a baseline data set. Plasma samples are subjected to lipid and metabolomic analyses. In addition, one percutaneous liver biopsy is performed on all monkeys immediately following collection of the baseline blood samples.

Monkeys that satisfy the initial screening criteria are started on a high saturated fat, high cholesterol diet augmented with refined sugar. Each animal is offered approximately 120 g per day of a diet of standard monkey chow (TekLad, Madison, Wis.) premixed with melted lard containing supplementary cholesterol and sucrose to deliver approximately 200 mg of cholesterol and 15 grams of saturated fat per day. The diet will be continued for a 10-week period, with weekly plasma collections. Plasma samples will undergo lipid and metabolome profiling. Serum lipid (e.g., total cholesterol, lipoproteins, triglycerides) and glucose parameters, as well as other metabolites (through LC-MS/MS metabolomic analysis) and liver enzyme levels (to determine toxicity) are assessed. Clinical hematology parameters are determined Biopsies of liver are taken at baseline and end points of the study as described below. These samples are subjected to analysis of expression of miR-33a, miR-33b, SREBP-1c, SREBP-2, ABCA1 and other potential miR-33 targets (e.g., AMPKalpha1, CROT, HADHB, SIRT6, etc.), as well as SREBP target genes (e.g., FASN, SCD1, ELOVL6, LDLR, HMG-CoA reductase, etc.). Candidate immunoblotting (e.g., ABCA1, AMPKa1, SIRT6, etc.) is also carried out on the liver biopsies to further verify effects on miR-33a/b targets. DNA microarray analysis is carried out on the liver samples to provide unbiased assessment of whole genome expression in response to diet-induced insulin resistance. Comprehensive statistical analysis of plasma data and qRT-PCR/microarray expression data is conducted. Descriptive statistical analysis is applied to clinical chemistry data.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method comprising:
    determining the level of triglycerides in a subject; and
    administering a therapeutically effective amount of an inhibitory nucleic acid that is complementary to SEQ ID NOs. 1 or 2 to a subject determined to have a fasting level of triglycerides greater than 150 mg/dL;
    whereby the level of serum and stored triglycerides in the subject is reduced.

2. The method of claim 1, wherein the therapeutically effective amount of an inhibitory nucleic acid that is complementary to SEQ ID NOs: 1 or 2 is administered to a subject determined to have a fasting level of triglycerides greater than 200 mg/dL.

3. The method of claim 1, wherein the subject is in need of treatment or a reduction of the risk of developing type 2 diabetes, metabolic syndrome, diabetic neuropathy, non-alcoholic fatty liver disease, non-alcoholic steatohepatitis, hepatocellular carcinoma, or cardiovascular disease.

4. The method of claim 1, wherein the subject is in need of a reduction of obesity.

5. The method of claim 1, wherein the inhibitory nucleic acid is an antisense oligonucleotide.

6. The method of claim 5, wherein the antisense oligonucleotide comprises SEQ ID NO:3.

7. The method of claim 5, wherein the antisense oligonucleotide comprises SEQ ID NO. 4.

8. The method of claim 5, wherein the antisense oligonucleotide is an antagomir.

9. The method of claim 1, wherein the inhibitory nucleic acid comprises at least one locked nucleoside.

10. The method of claim 1, wherein the inhibitory nucleic acid is an interfering RNA.

11. The method of claim 9, wherein the interfering RNA is a small hairpin RNA (shRNA) or small interfering RNA (siRNA).

12. The method of claim 1, wherein the inhibitory nucleic acid sequence inhibits post-transcriptional processing of SEQ ID NO.1 or 2.

13. The method of claim 1, wherein the subject has or is at risk of developing metabolic syndrome or Type 2 diabetes.

14. The method of claim 13, further comprising selecting a subject on the basis that they have or are at risk of developing metabolic syndrome or Type 2 diabetes.

15. The method of claim 4, further comprising selecting a subject who is in need of weight loss.

16. The method of claim 4, wherein the subject is selected if they have a BMI of 25 or above.

* * * * *

SEQUENCE LISTING

```
<160> NUMBER OF SEQ ID NOS: 4

<210> SEQ ID NO 1
<211> LENGTH: 21
<212> TYPE: RNA
<213> ORGANISM: Homo sapiens

<400> SEQUENCE: 1
gugcauugua guugcauugc a                                              21

<210> SEQ ID NO 2
<211> LENGTH: 20
<212> TYPE: RNA
<213> ORGANISM: Homo sapiens

<400> SEQUENCE: 2
gugcauugcu guugcauugc                                                20

<210> SEQ ID NO 3
<211> LENGTH: 21
<212> TYPE: RNA
<213> ORGANISM: Artificial Sequence
<220> FEATURE:
<223> OTHER INFORMATION: synthetically generated oligos

<400> SEQUENCE: 3
ugcaaugcaa cuacaaugca c                                              21

<210> SEQ ID NO 4
<211> LENGTH: 20
```

-continued

```
<212> TYPE: RNA
<213> ORGANISM: Artificial Sequence
<220> FEATURE:
<223> OTHER INFORMATION: synthetically generated oligos

<400> SEQUENCE: 4
gcaaugcaac agcaaugcac                                              20
```